United States Patent [19]
Freedman

[11] Patent Number: 6,126,596
[45] Date of Patent: Oct. 3, 2000

[54] APPARATUS AND METHOD FOR EVALUATING A CLIENT'S CONDITION AND THE CONCORDANCE OF A CLINICIAN'S TREATMENT WITH TREATMENT GUIDELINES

[76] Inventor: Joshua Freedman, 235 Main St. #218, Venice, Calif. 90291

[21] Appl. No.: 08/867,297

[22] Filed: Jun. 2, 1997

[51] Int. Cl.[7] .................................................... A61B 5/00
[52] U.S. Cl. ........................................... 600/300; 128/920
[58] Field of Search .................................... 600/300, 301; 128/900, 923, 924, 897

[56] References Cited

U.S. PATENT DOCUMENTS

| | | | |
|---|---|---|---|
| 5,435,324 | 7/1995 | Brill | 128/899 |
| 5,619,991 | 4/1997 | Sloane | 600/300 |

OTHER PUBLICATIONS

Barnett, G. O. et al., "Quality Assurance through Automated Monitoring and Concurrent Feedback Using a Computer-–Based Medical Information System," Medical Care, vol. XVI, No. 11, pp. 962–970, Nov. 1978.

Banks, N. J. et al., "Improving the Quality of Ambulatory Health Care with Enhanced Medical Information Systems: Using the Computer to Diagnose Faulty Clinical Processes," Journal of Medical Systems, vol. 14, pp. 345–349, Jun. 1990.

*Primary Examiner*—Cary E. O'Connor
*Assistant Examiner*—Eric F. Winakur
*Attorney, Agent, or Firm*—Blakely Sokoloff Taylor & Zafman

[57] ABSTRACT

A system that can collect data, directly from a client and use this data both to diagnose and to establish the severity of a client's condition. The system can also use this data to look-up one or more appropriate treatments according to treatment guidelines stored in its memory. It then uses this information to monitor if the treatment decisions made by the treating clinician or other medical provider is consistent with the stored treatment guidelines. The system can suggest treatments to the medical provider, inform the provider if the provider chooses a treatment or treatments that do not follow the treatment guidelines, require the provider to actively over-ride the treatment guidelines or require the provider to obtain agreement to over-ride from a supervisor. Additionally, the system can store information on treatments that do not follow the treatment guidelines for ongoing review of provider performance by provider supervisors.

15 Claims, 27 Drawing Sheets

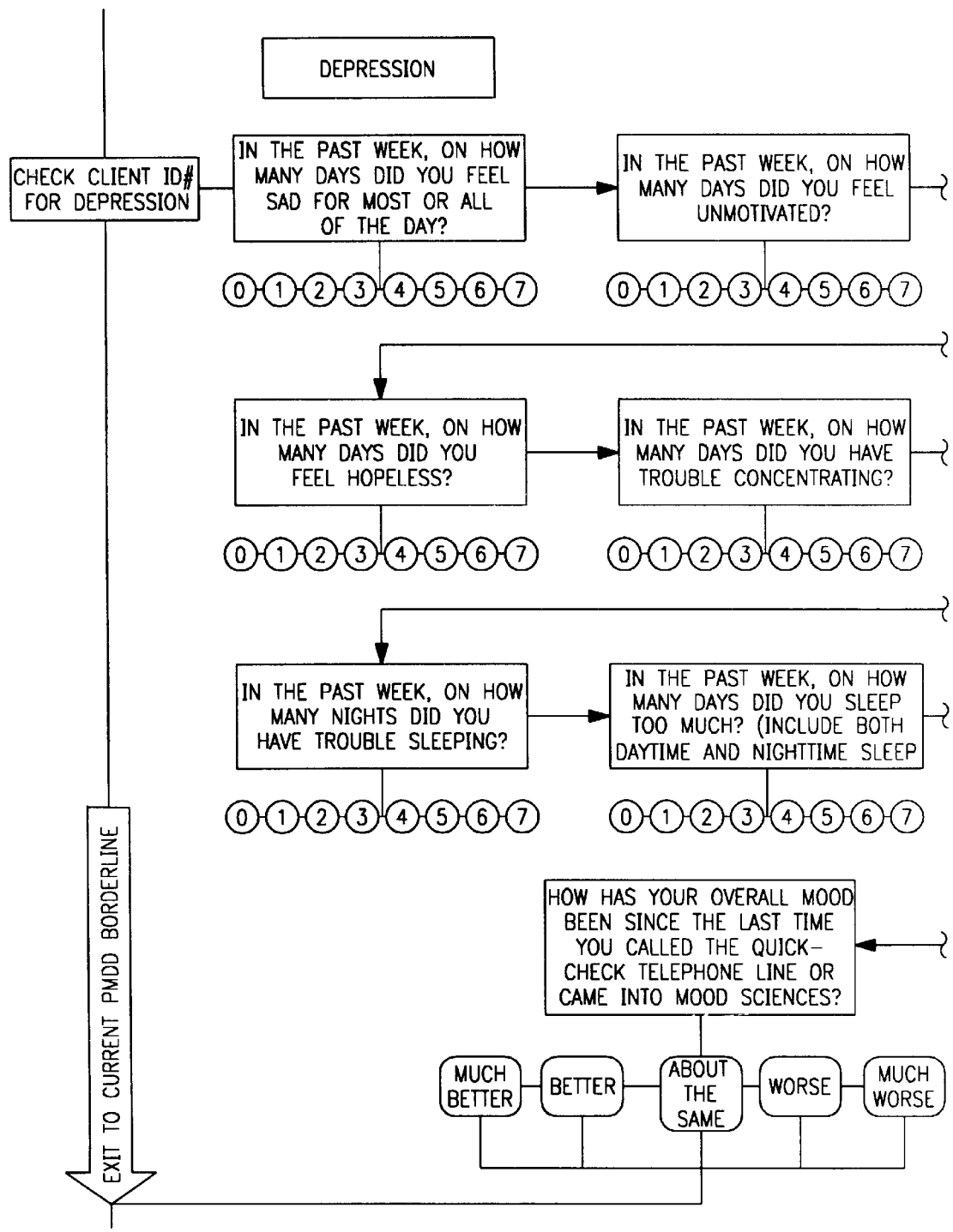
FIG. 5b-I

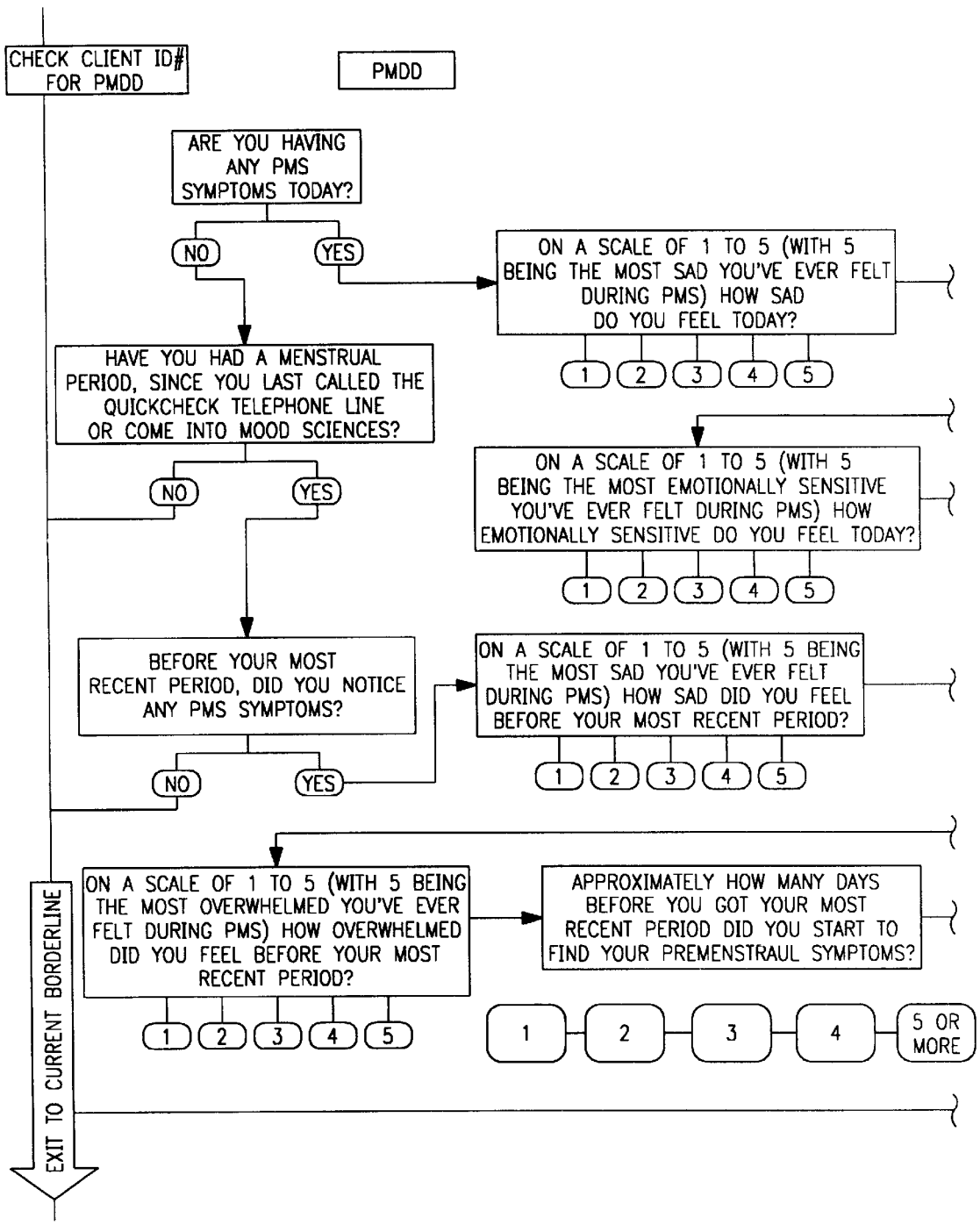
FIG. 5c-I

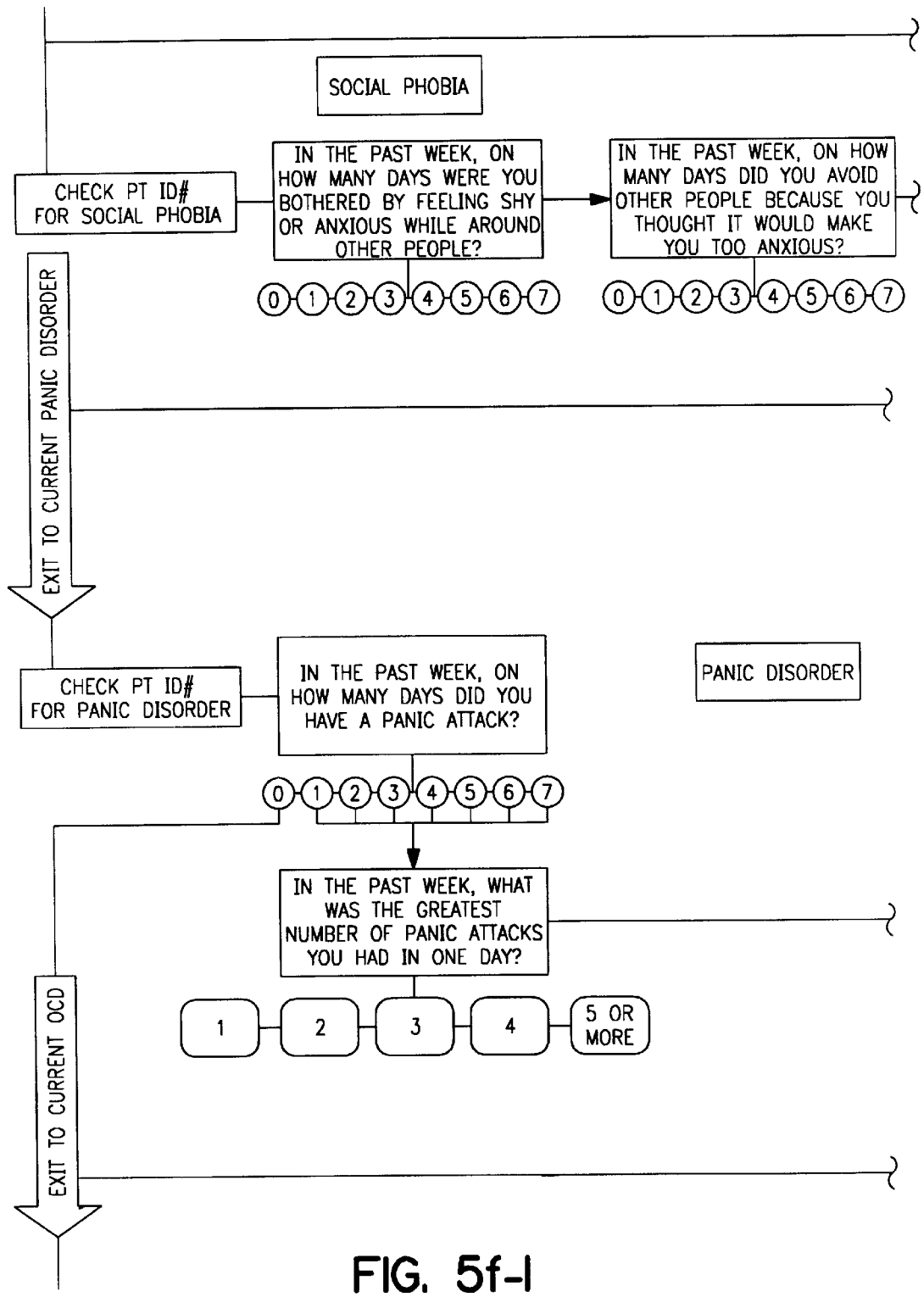
FIG. 5f-I

APPARATUS AND METHOD FOR EVALUATING A CLIENT'S CONDITION AND THE CONCORDANCE OF A CLINICIAN'S TREATMENT WITH TREATMENT GUIDELINES

BACKGROUND OF THE INVENTION

1. Field of the Invention

The present invention relates to a computer based system that diagnoses, establishes severity, and monitors a client's condition and also monitors medical decisions made by the clinician treating the client.

2. Description of Related Art

As shown and discussed in U.S. Pat. Nos. 5,553,609; 5,601,435; 5,471,382; 5,572,421; 5,341,291; 5,558,638; 5,517,405; 5,357,427 and 5,390,238 computer systems are frequently used in the medical industry to collect data. Some of these systems allow data to be collected from a client that is at a location remote from the clinician or other medical personnel. The remotely collected data can be reviewed by clinicians to generate a course of treatment. Even when using computer collected data, however, clinicians may select treatment that diverges from recommended treatment guidelines; to date, no system uses data not entered by the clinician to monitor clinician decisions for concordance with treatment guidelines.

U.S. Pat. No. 5,473,537 issued to Glazer et al. discloses a system and method for collecting psychiatric data and then providing a recommended course of treatment. The data is provided by a client who responds to a number of questions. The recommended treatment is determined from a complex matrix that contains numerical values that are associated with the client's answers. The clinician may review and follow the recommended treatment. The Glazer system still allows the clinician to ignore the recommended treatment and prescribe a different treatment. The Glazer system does not monitor the treatment prescribed by the clinician, and is unable to use treatment guidelines interactively to guide medical decisions. Hence, a clinician may choose to ignore the treatment guidelines and the Glazer system neither records this nor attempts to influence such choices.

To date there has not been developed a system which can both evaluate a client's condition and monitor a treatment prescribed by a clinician. Such a system would be particularly desirable for a Health Maintenance Organization (HMO) that is attempting to provide care according to recommended treatment guidelines. It would therefore be desirable to provide a computer-based system that attempts to influence treatment decisions and is capable of requiring real-time supervisory accession to decisions that diverge from or are not covered by the treatment guidelines.

Traditionally, clinicians diagnose clients based on information obtained in an initial interview. Usually, this information is obtained neither completely nor consistently. Increasingly, medical diagnosis is established based on evaluating the client's condition according to accepted criteria. For example, a clinician should determine if a client has a Major Depression Episode (MDE) by establishing if the client meets the criteria described in the consensus document establishing these criteria, the Diagnostic and Statistical Manual-IV.

It would be desirable to provide a computer based system that could provide a single questionnaire that is used both to diagnose and to determine the severity of the client's condition. Currently, after determining a diagnosis, if a clinician wishes to quantitatively determine the severity of the condition, they must use a separate instrument to measure severity for that diagnosis. In the case of MDE, for example, the clinician might use the Hamilton Rating Scale for Depression (HRS-D) because many diagnostic measures, including the DSM-IV, do not provide a quantitative measure of severity of a diagnosis. Similarly, many severity measures, including HRS-D, do not establish a diagnosis.

SUMMARY OF THE INVENTION

The present invention is a system which can monitor how congruent a medical provider's treatment decisions are with treatment guidelines, including providing real-time alerts and mandatory review in the case of divergent decisions. The system includes a first terminal that allows a client to enter data in response to questions, and a second terminal at which a clinician can review the data, enter additional data, and enter a medical decision into the system. The system uses the data to look up recommended treatment from treatment guidelines stored in its memory, and reports those treatments that are consistent with the guidelines. The system also compares the medical decision entered by the clinician to the recommendation the system retrieved from the treatment guidelines.

The system can warn the clinician regarding treatment decisions that deviate from prescribed treatment guidelines; it can allow the clinician to override the guidelines after entering additional information; and it can, in some cases, require a clinician's supervisor to enter a password before the clinician may implement medical decisions that deviate from standard treatment guidelines.

DETAILED DESCRIPTION OF THE INVENTION

Figure 1:
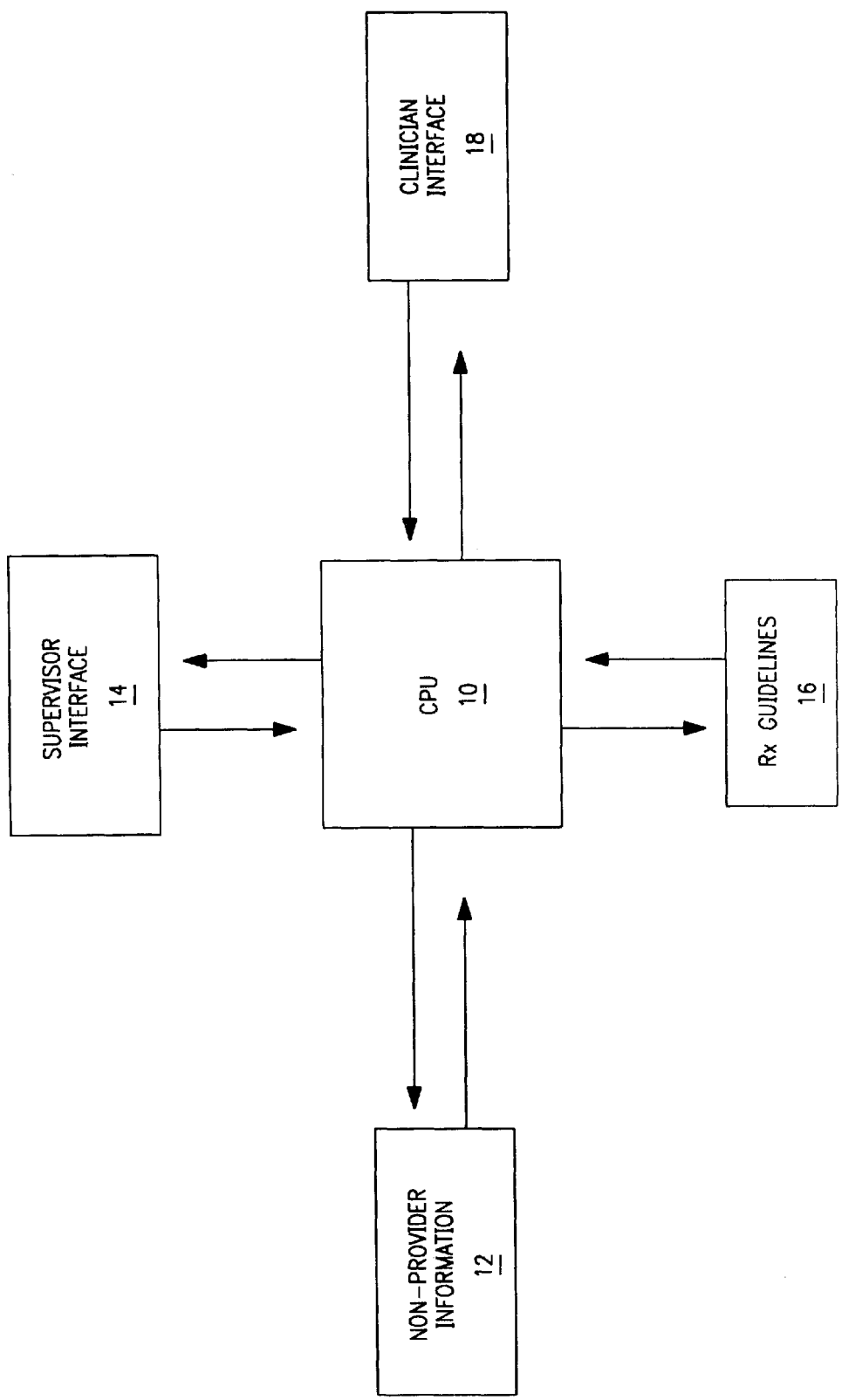
FIG. 1 is a flowchart showing how the present invention reviews and monitors data.

Referring to the drawings more particularly by reference numbers, FIG. 1 shows an overview of the present invention. The system is used to obtain non-provider information, compare the information with treatment and monitoring guidelines, guide clinician medical decisions, and require supervisor approval for decisions that deviate from standard guidelines. The non-provider information 12 may be client-entered self-report, laboratory data, or diagnostic tests and other reports. The non-provider information 12 is compared with treatment guidelines 16. The clinician interface 18 may provide the following functions: allow a clinician to enter additional information, provide a graphical display of data reports, report recommended treatment according to treatment guidelines, alert clinician of deviations from guidelines with explanations, allow a clinician to override treatment guidelines either with or without supervisor signoff. The supervisor interface 14 displays alerts for treatment decisions that require sign-off, and provides monitoring data on consistency of clinician treatment with treatment guidelines. If the non-provider information 12 is client-entered self report, the system is also used to generate a diagnosis and severity level for client's condition.

Figure 2:
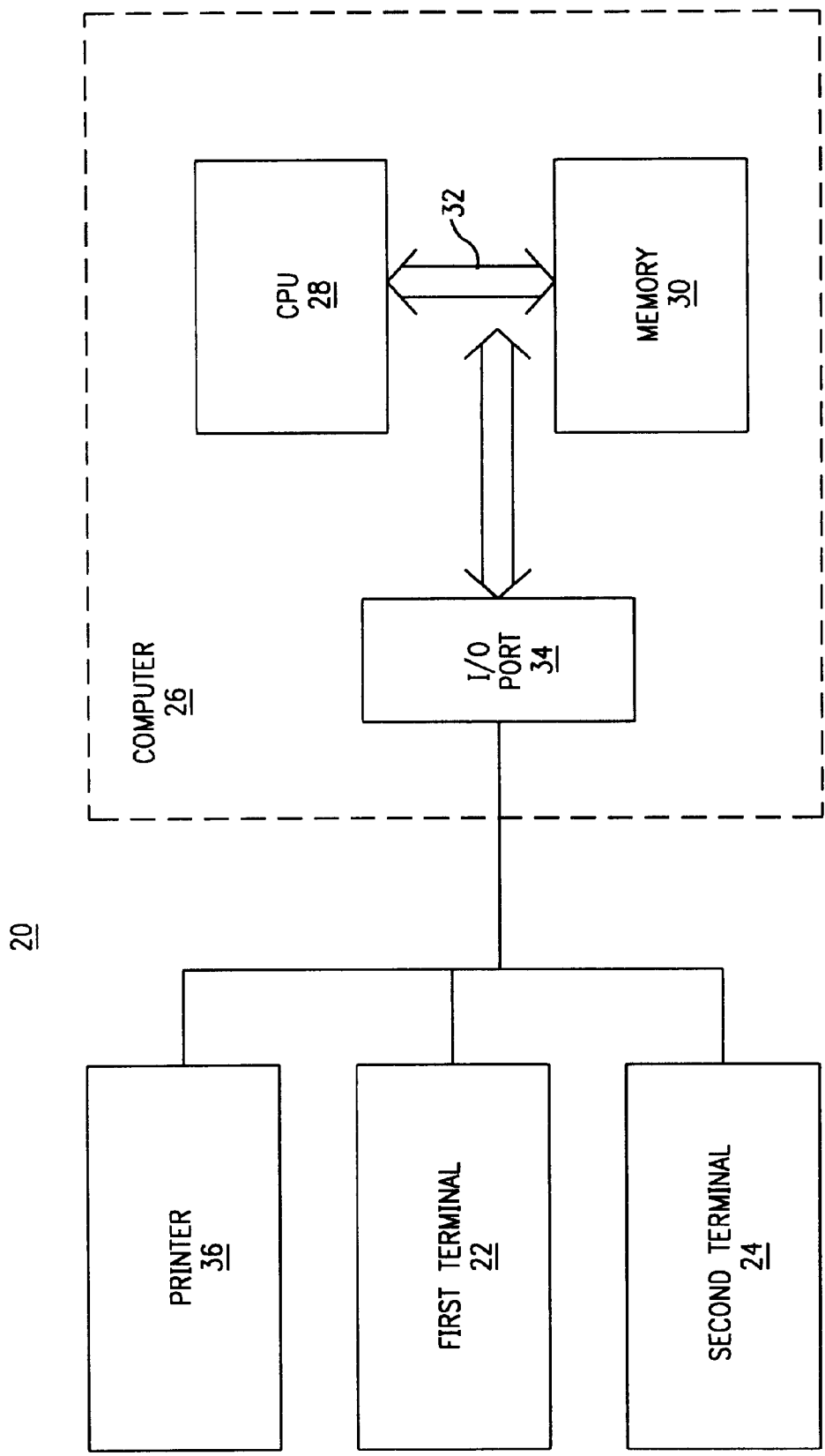
FIG. 2 is a schematic of the present invention.

By way of example, FIG. 2 demonstrates how the system 20 may be used to query clients to enter information, collect data, evaluate a client's condition and monitor medical decisions made by a clinician.

The system 20 may include a first terminal 22 which may query a client to enter data in response to questions displayed by the terminal 22. The system 20 may also have a second terminal 24 which may display client responses and highlight suggested treatments based on treatment guidelines stored in memory; it also may allow a clinician to review the data and select a treatment decision. The terminal 24 may display an alert if the treatment decision selected by the clinician is inconsistent with treatment guidelines stored in memory, and may require supervisory approval prior to implementation.

The system 20 includes a computer 26 comprised of a central processing unit (CPU) 28 that is connected to memory 30 by a bus 32. An Input-ouput port (I/O Port) 34 receives the data generated from CPU 28 and entered from terminals 22 and 24, and provides information which is displayed by the terminals 22 and 24. The terminals 22 and 24 may be remotely linked to the computer 26. The system 20 of the present invention allows a client to enter data without having to be physically present at the facility of the clinician. By way of example, the terminals 22 and 24, and computer 26 may be linked by a LAN or WAN system.

The memory 30 typically includes both random access memory (RAM) and read only memory (ROM). The memory 30 may also include a mass storage medium such as a hard disk drive. The CPU 28 is connected to the input/output (I/O) port 34 by the bus 32. The I/O port 34 is connected to the terminals 22 and 24. The I/O port 34 may also be connected to a printer 36.

The CPU 28 performs routines and computations in accordance with instructions retrieved from memory 30. The instructions may be embedded in ROM, stored on the mass storage device and/or retrieved from an external source such as a floppy disk, or downloaded from a network through the I/O port 34. The CPU 28 may generate information such as questions that are provided to the terminals 22 and 24 through the I/O port 34 in accordance with the instructions of a software program. The CPU 28 may also process and store data that is entered through the terminals 22 and 24. The system 20 may query a client to enter data in response to questions displayed by the terminal 22. The system 20 may also display a client's responses to questions and highlight suggested decisions based on stored treatment guidelines at terminal 24. A clinician may choose treatment decisions and/or be required to obtain supervisory approval for treatment decisions that deviate from treatment guidelines stored in memory 30.

Figure 3A:
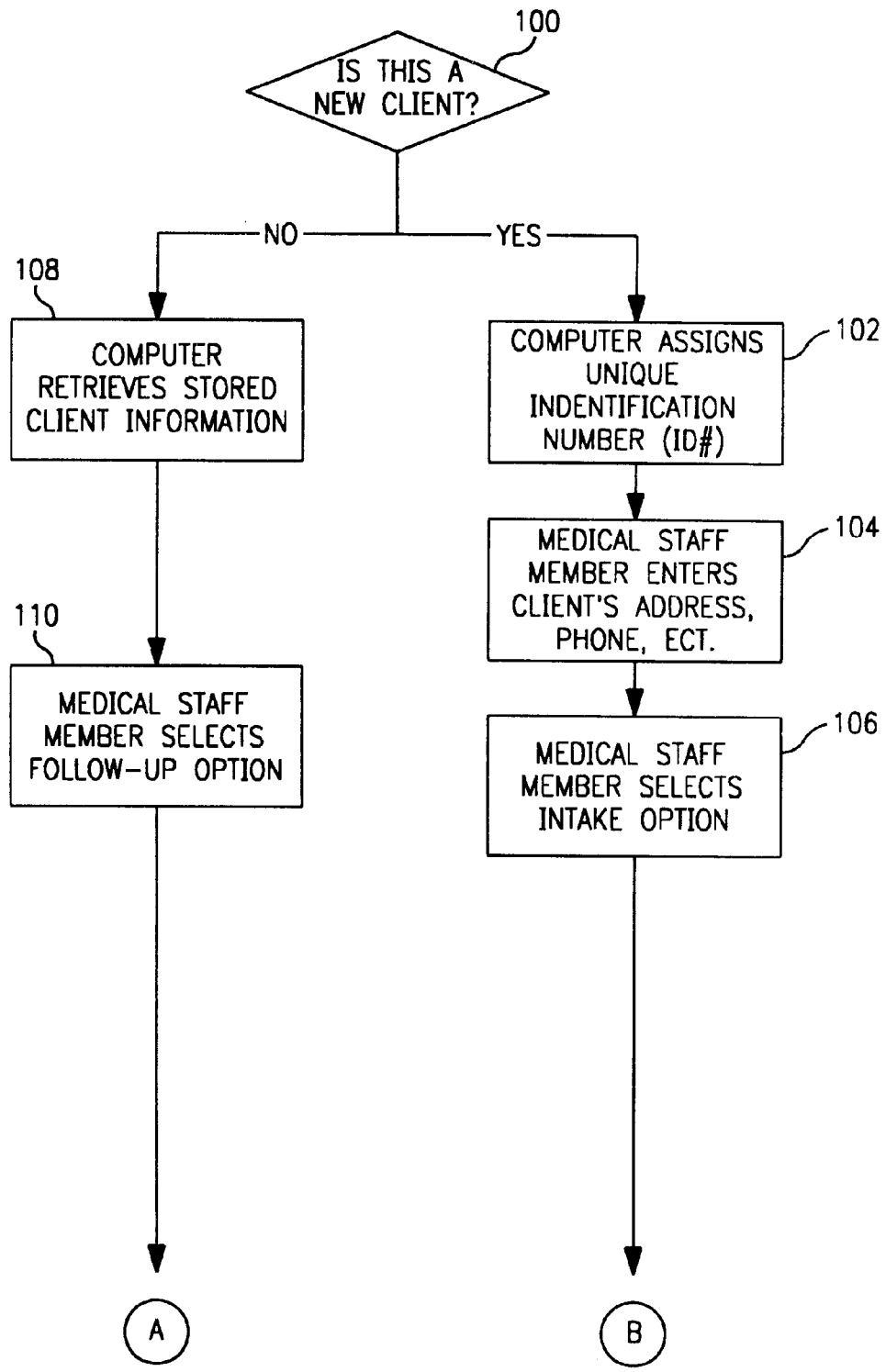
FIGS. 3a–b are flowcharts showing a sample client entering data into the system.
Figure 3B:
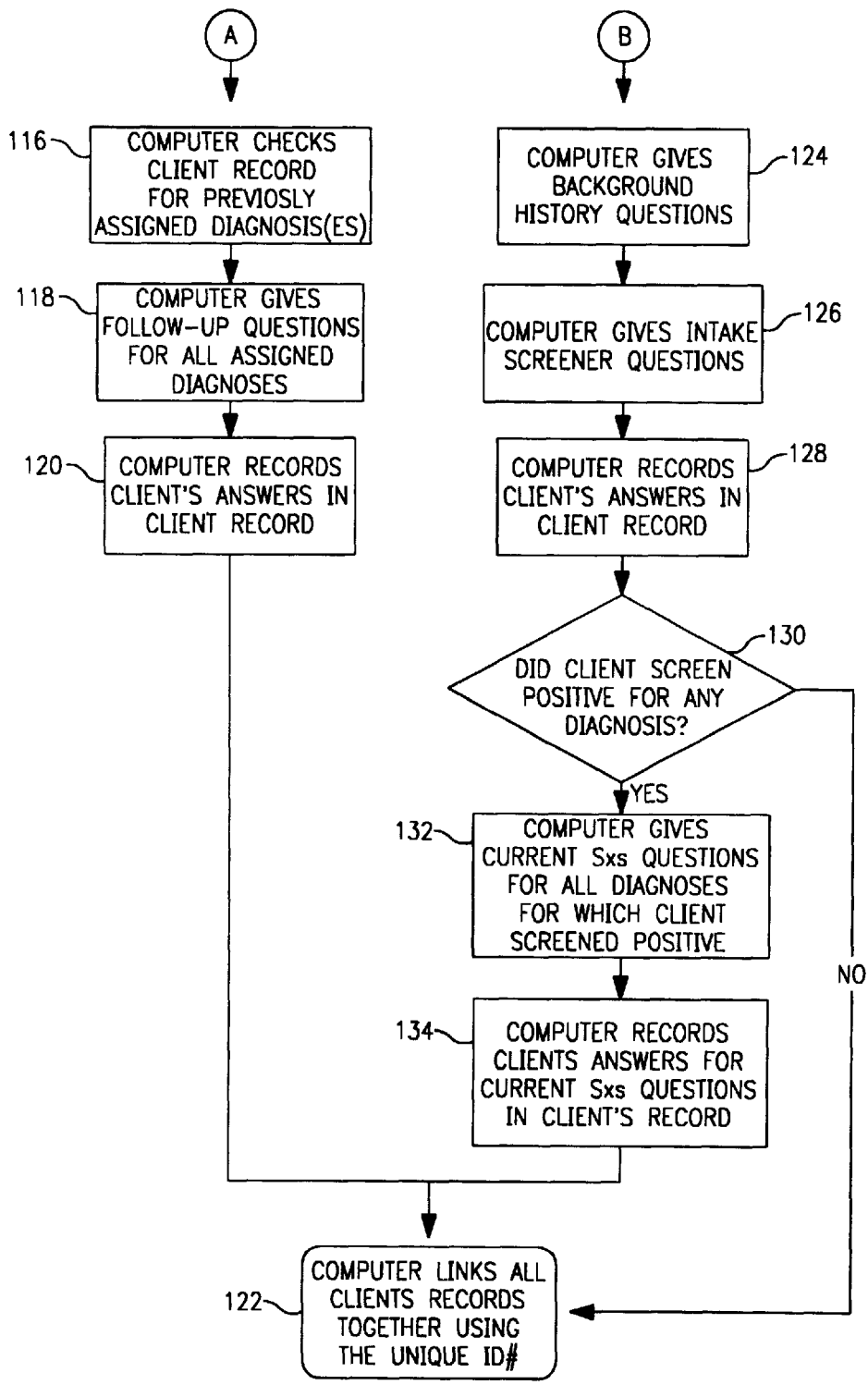

FIGS. 3a–b show a sample process for compiling psychiatric data on a client. In decision block 100 the client is queried as to whether they are in the system 20. If not, the computer assigns a unique identification number (ID) to the client and enters the client's personal information in blocks 102 and 104. A medical staff member then enters an intake option in block 106. The intake option relates to a series of questions that are asked of the client. If the client is not new, the computer 26 retrieves the client's personal information and the medical staff member enters a follow-up option in blocks 108 and 110, respectively.

If the medical staff member selects the follow-up option in block 110, the computer checks the records for a previously assigned diagnosis in block 116. In block 118, the client enters data in response to questions provided by the computer 26 relating to previously assigned diagnosis from block 116 and displayed by the first terminal 22. The computer 26 then stores the client's entered data in a record and links the record to the client's ID in blocks 120 and 122.

If the medical staff member selects the intake option from block 106, the process proceeds to blocks 124, 126 and 128. The client enters data in response to questions regarding background history and intake screener questions in blocks 124 and 126. The intake may include questions relating to a client's psychological state; for example, the client may be asked whether they are sad, etc.

The entered data is stored in a unique record based on the client ID in block 128. The process then determines whether the client answered any of the questions in the affirmative in decision block 130. If the client did not respond "yes" to any question, then the process proceeds to block 122 where the computer links all of the client's responses with the client ID. If the client does answer "yes", the system queries the client with further questions regarding current symptoms for all possible diagnoses in block 132. The client's responses are stored in client's unique record in block 134.

Figure 4A:
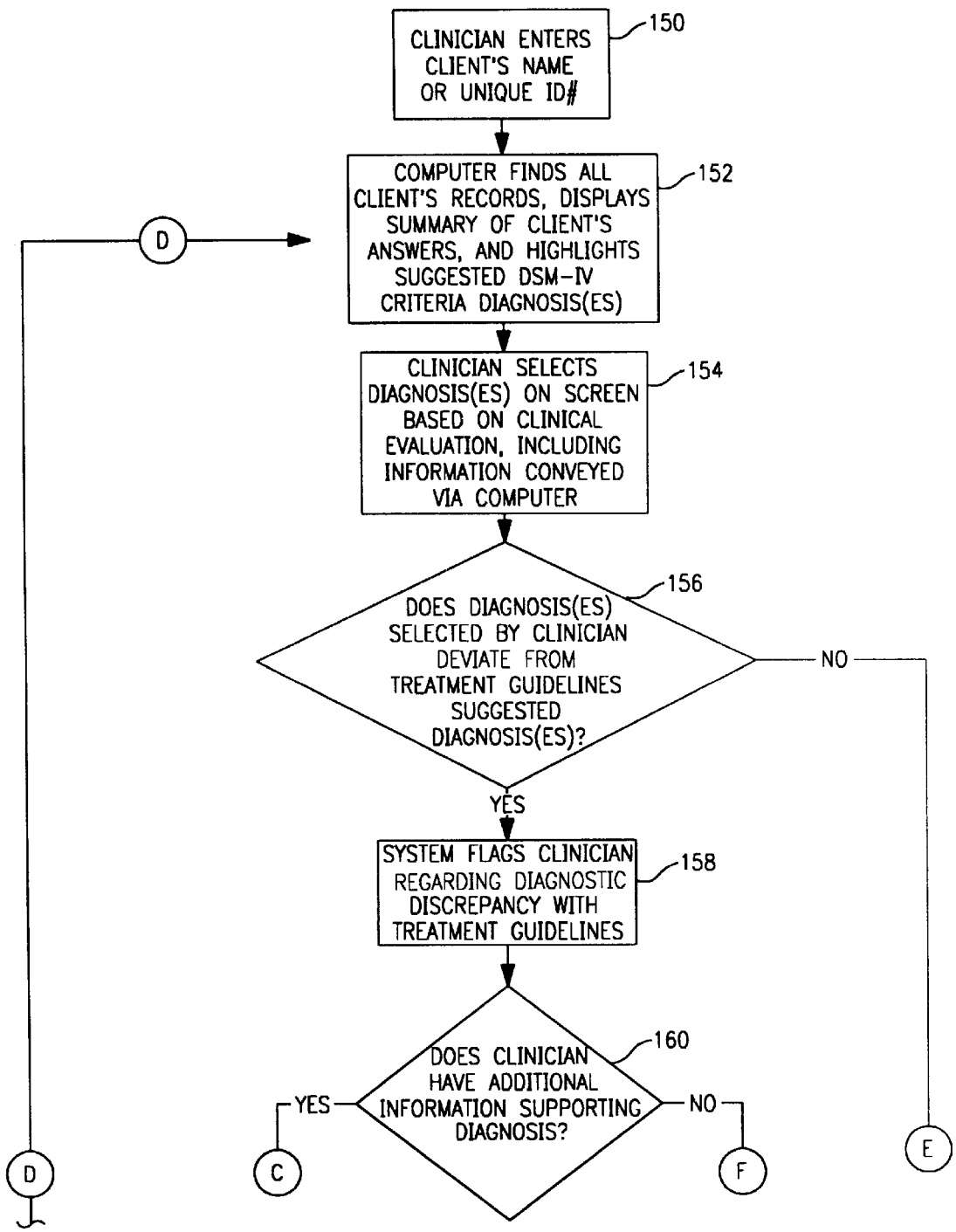
FIGS. 4a–c are flowcharts showing a clinician utilizing the system for a psychiatric client visit.
Figure 4B:
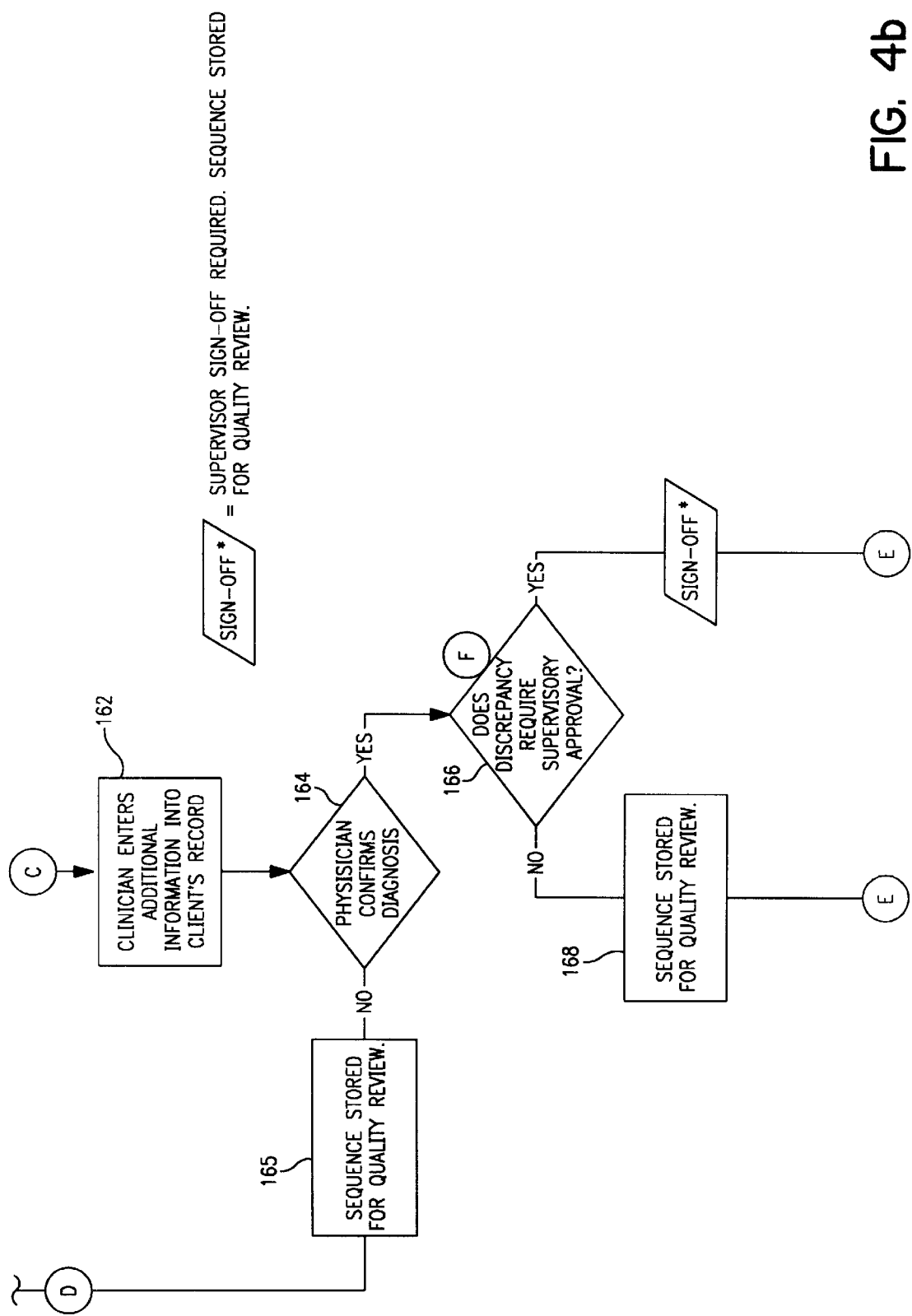
Figure 4C:
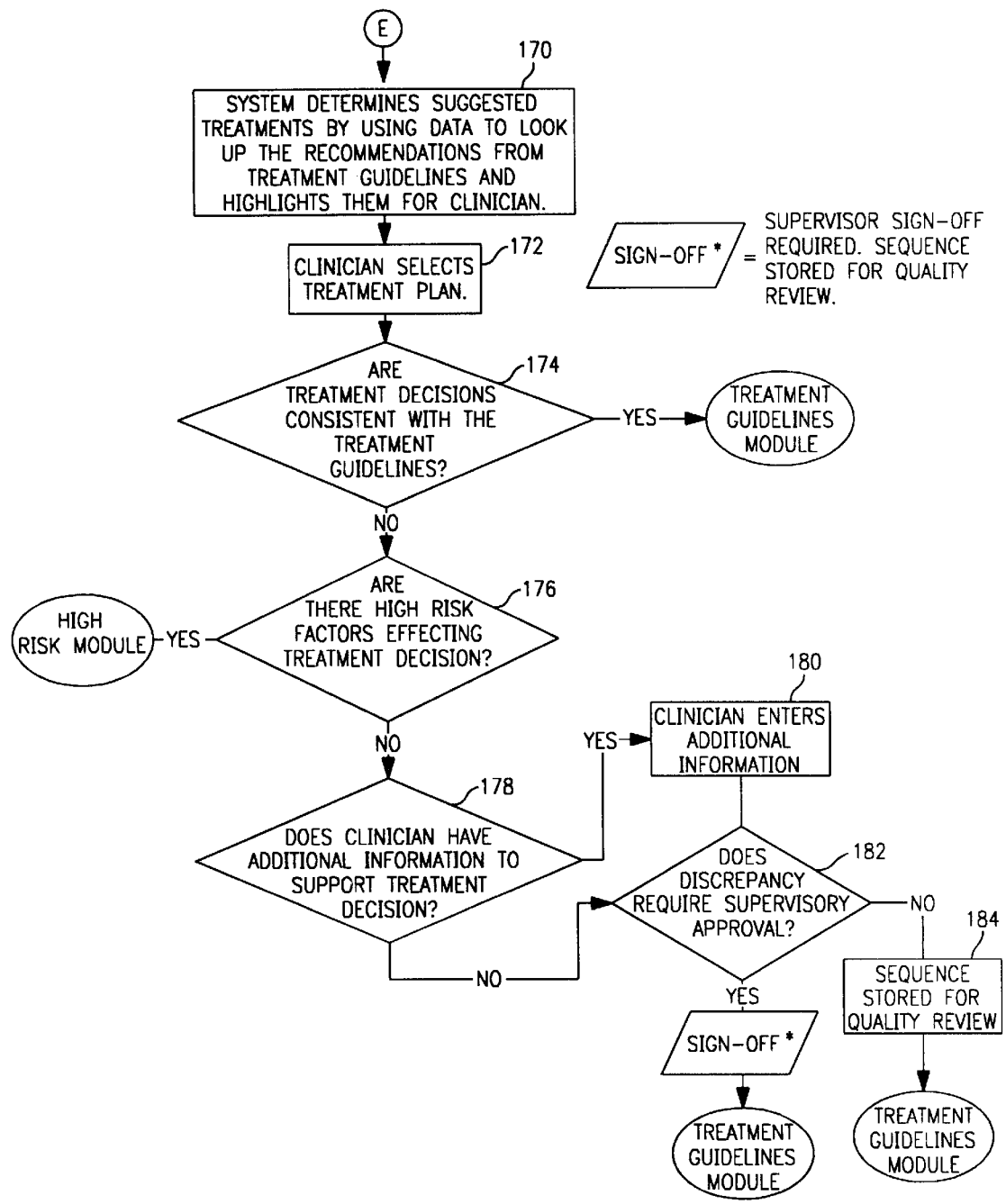
Figure 5A:
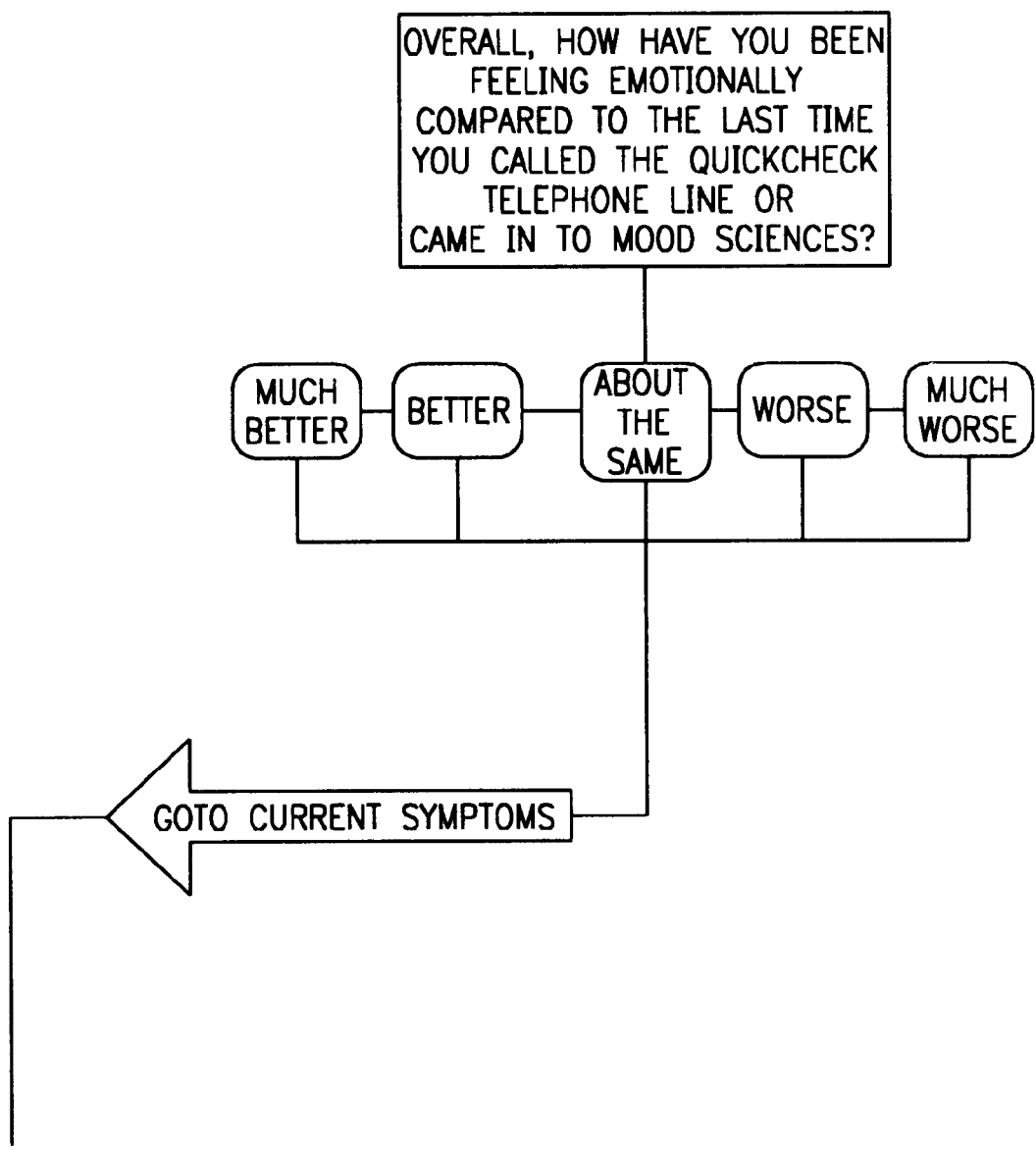
FIGS. 5a–j are flowcharts showing questions provided by the system.
Figures 2, 5B:
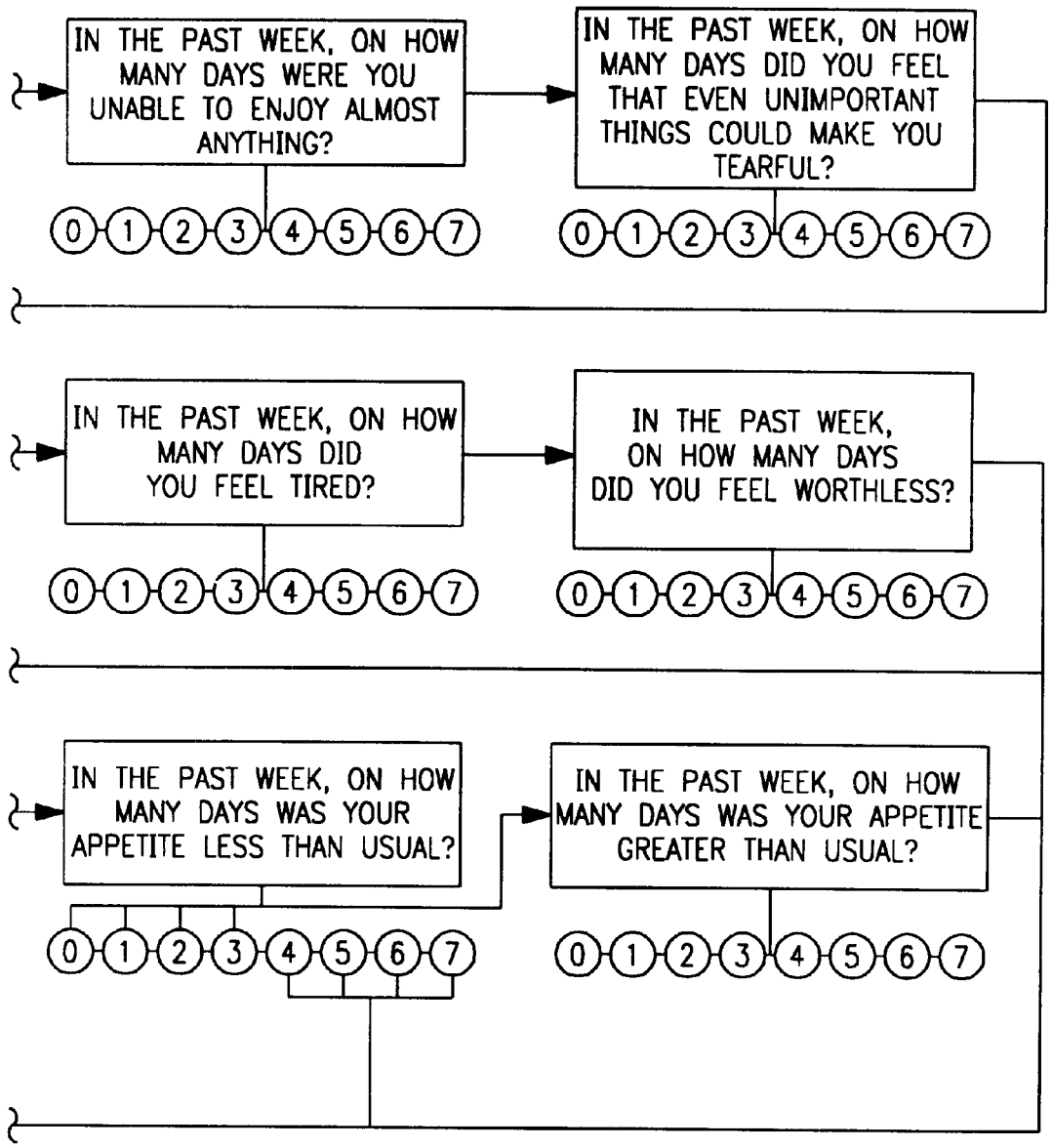
Figures 2, 5C:
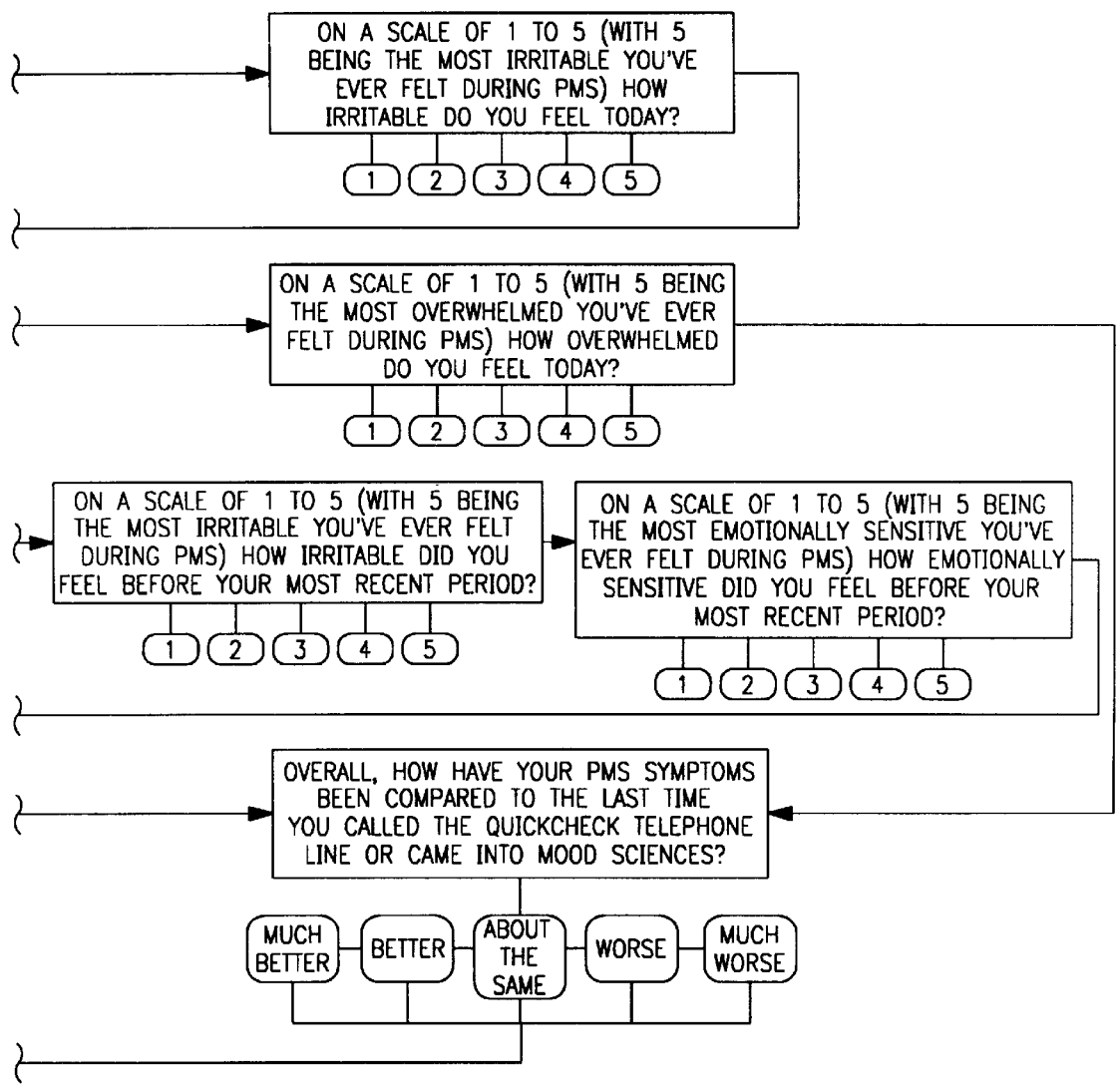
Figure 5D:
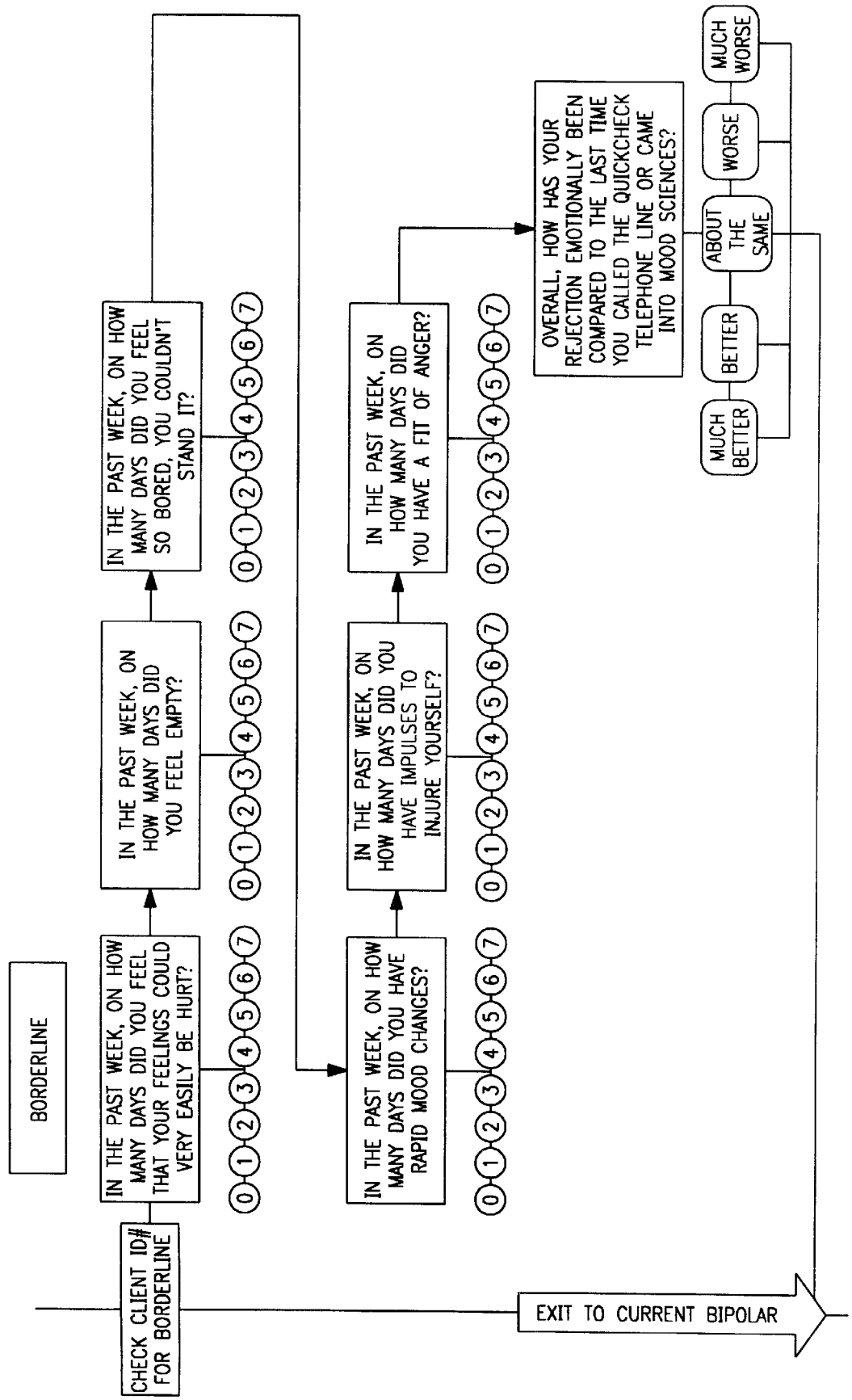
Figures 1, 5E:
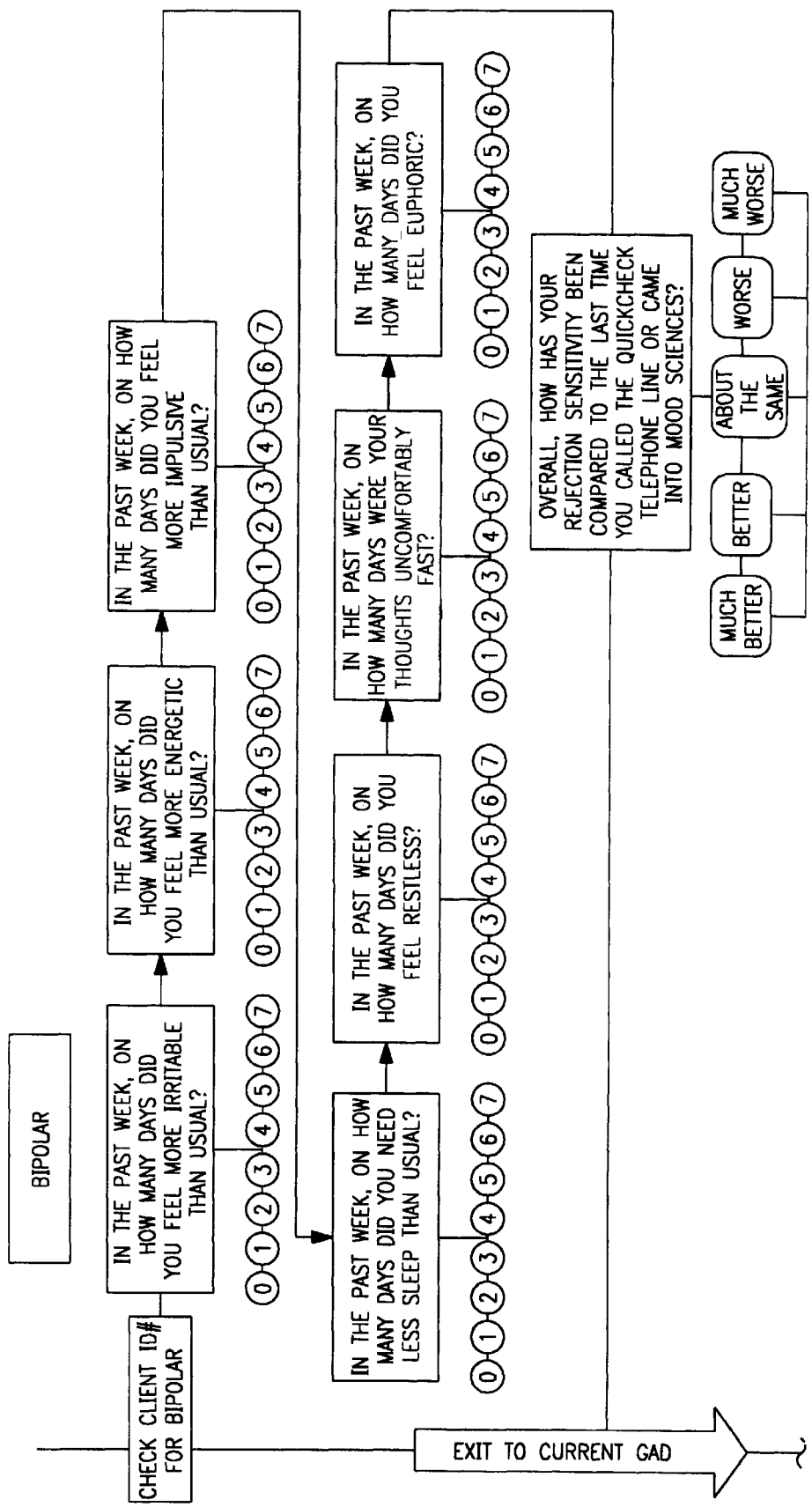
Figures 2, 5E:
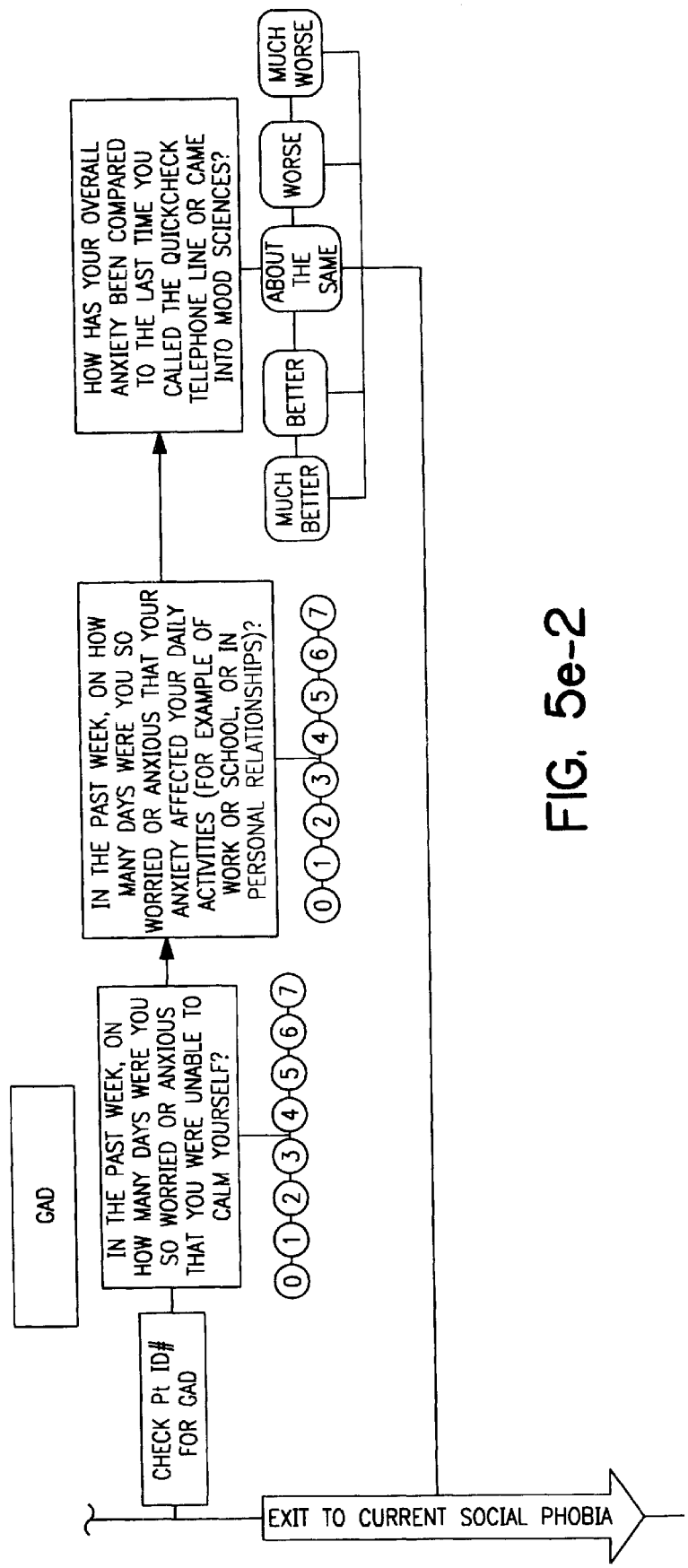
Figures 2, 5F:
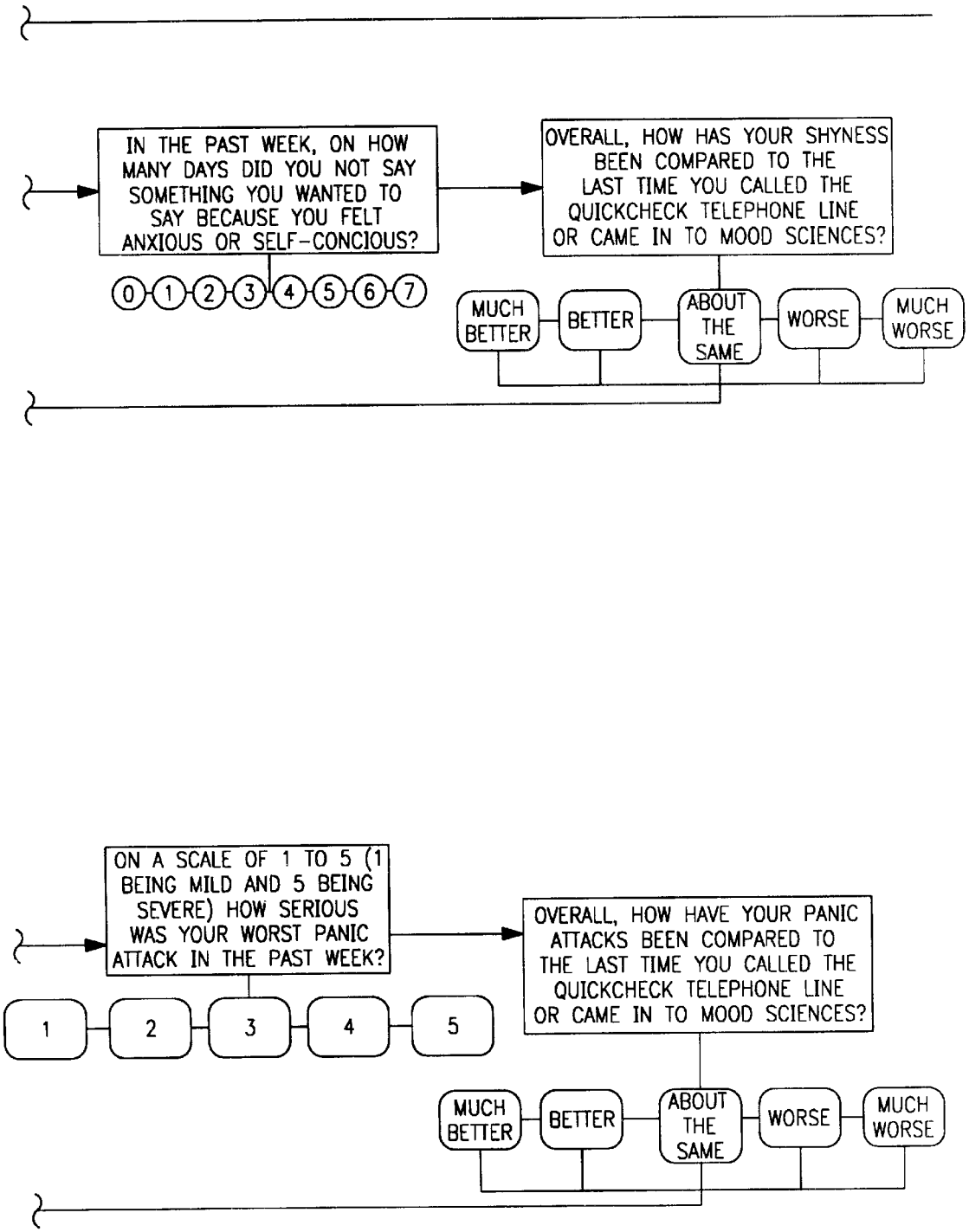
Figures 1, 5G:
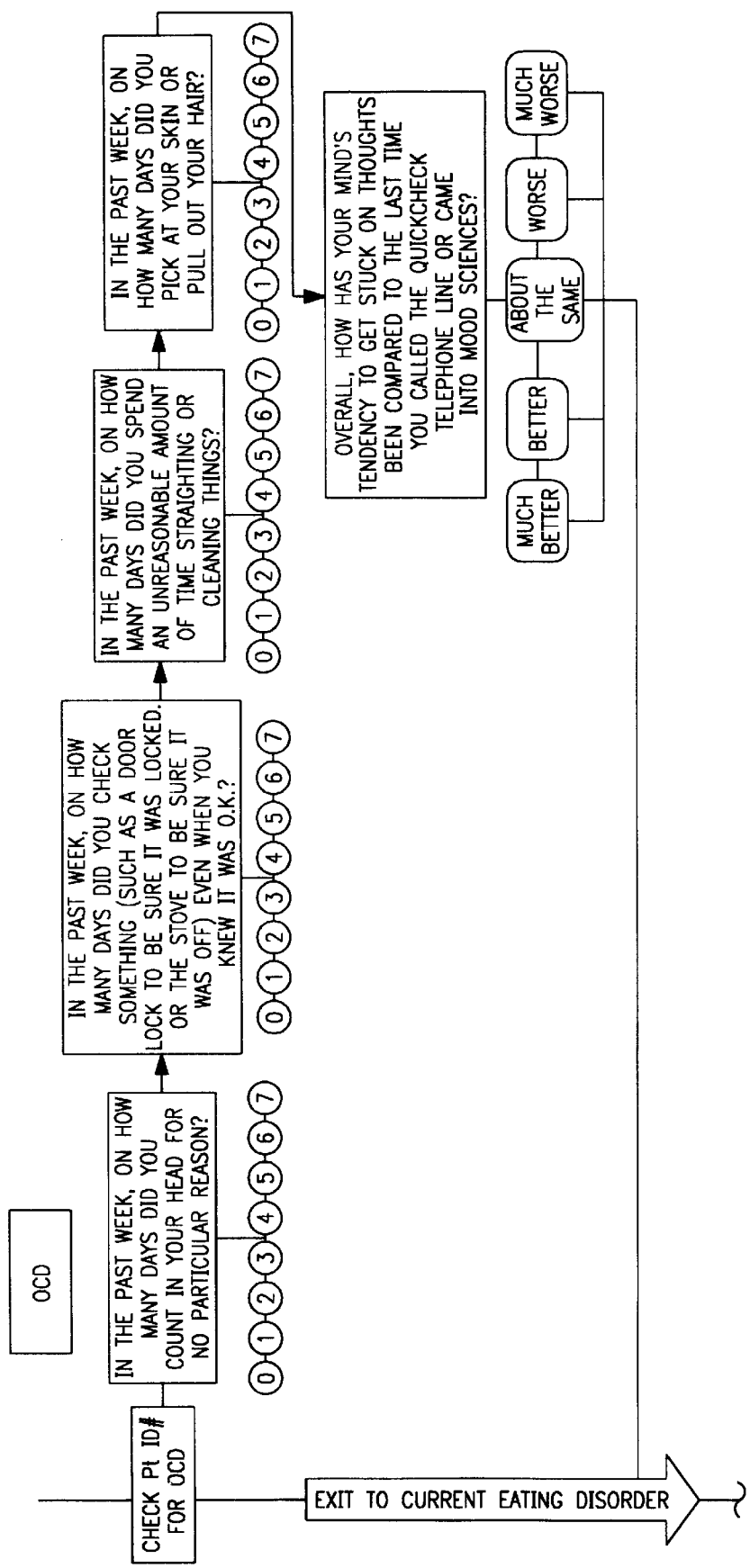
Figures 2, 5G:
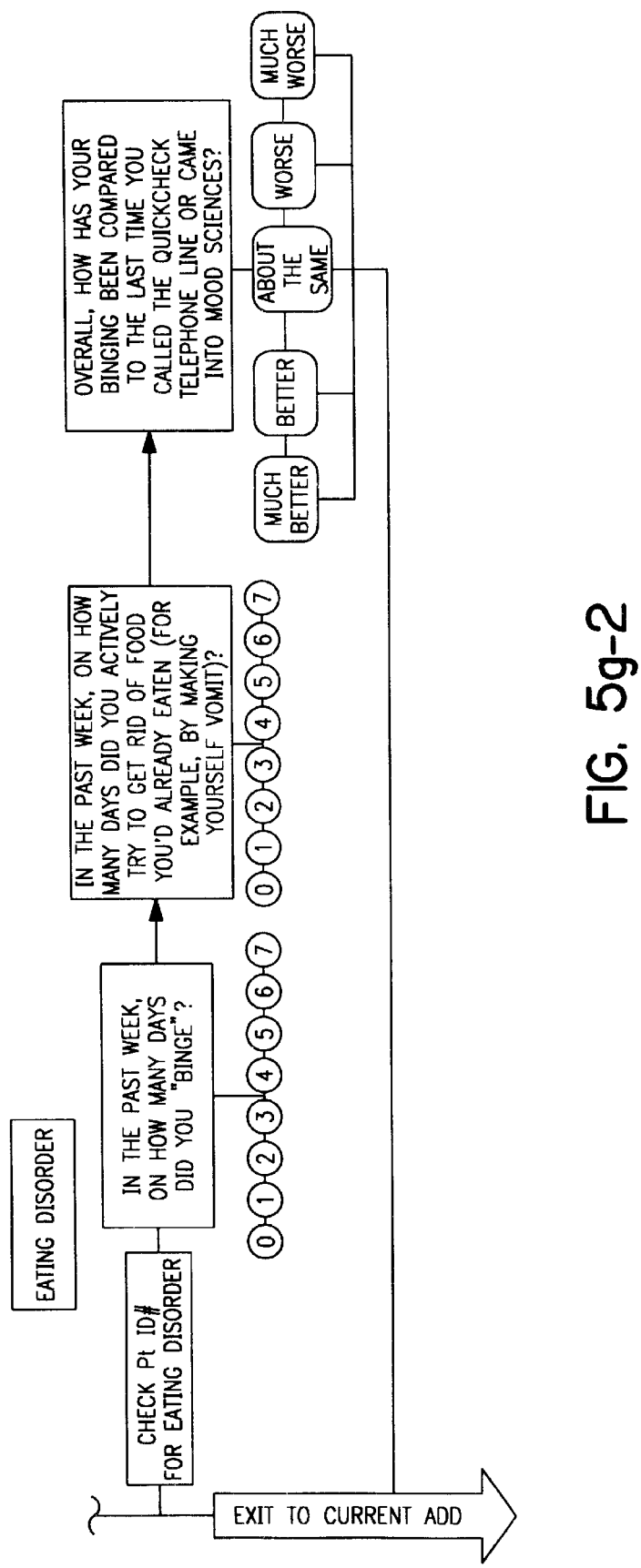
Figure 5H:
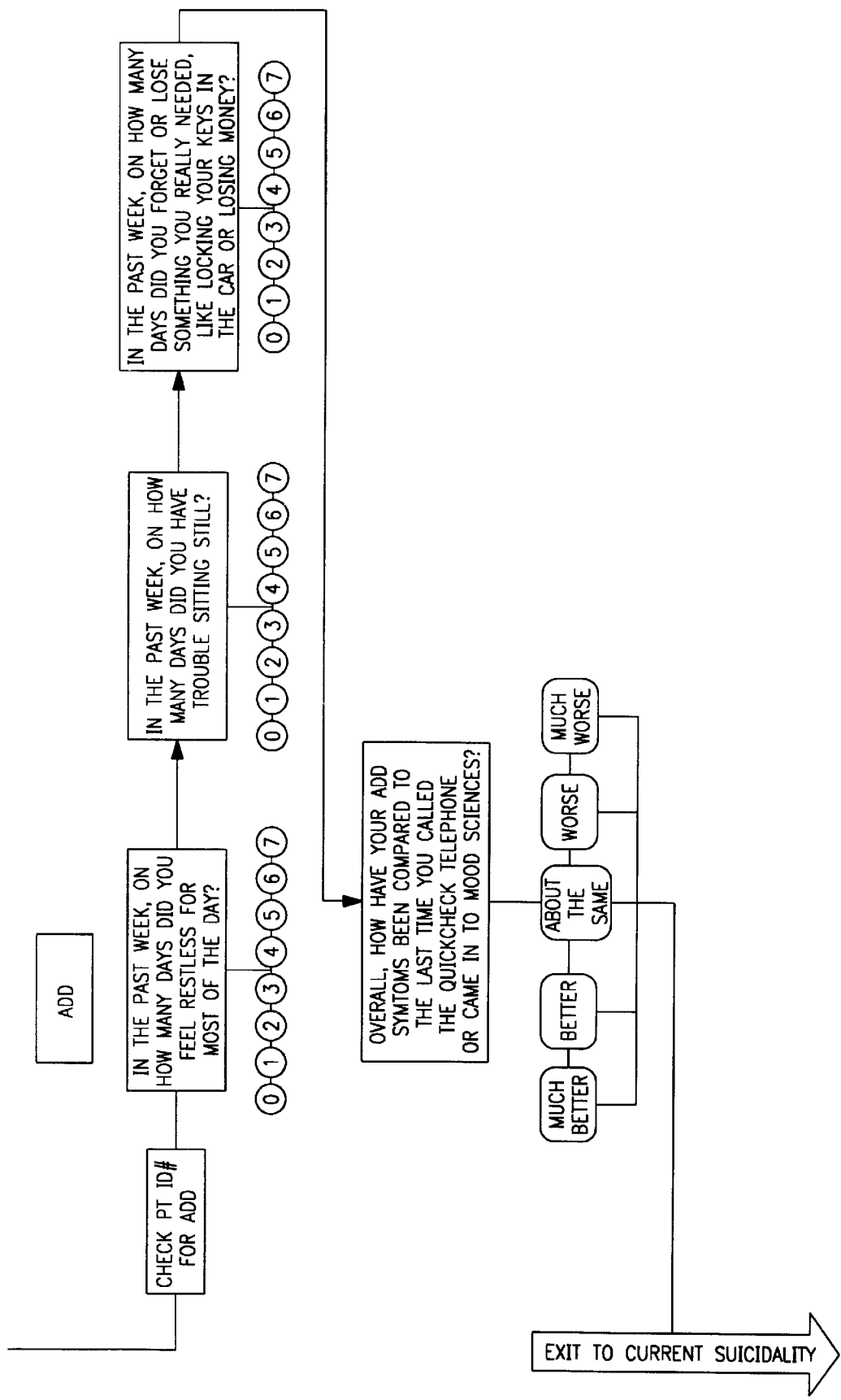
Figure 5I:
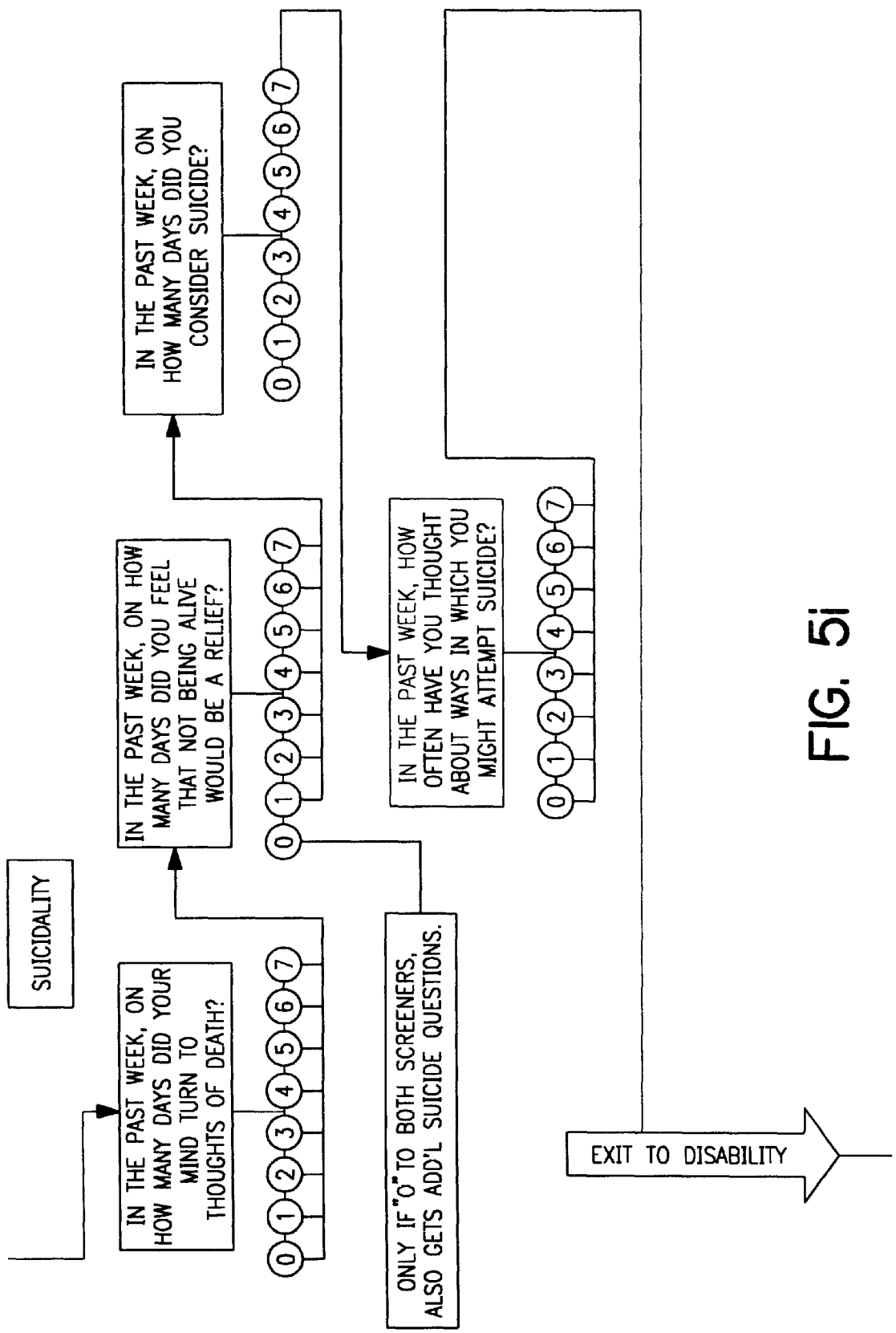
Figure 5J:
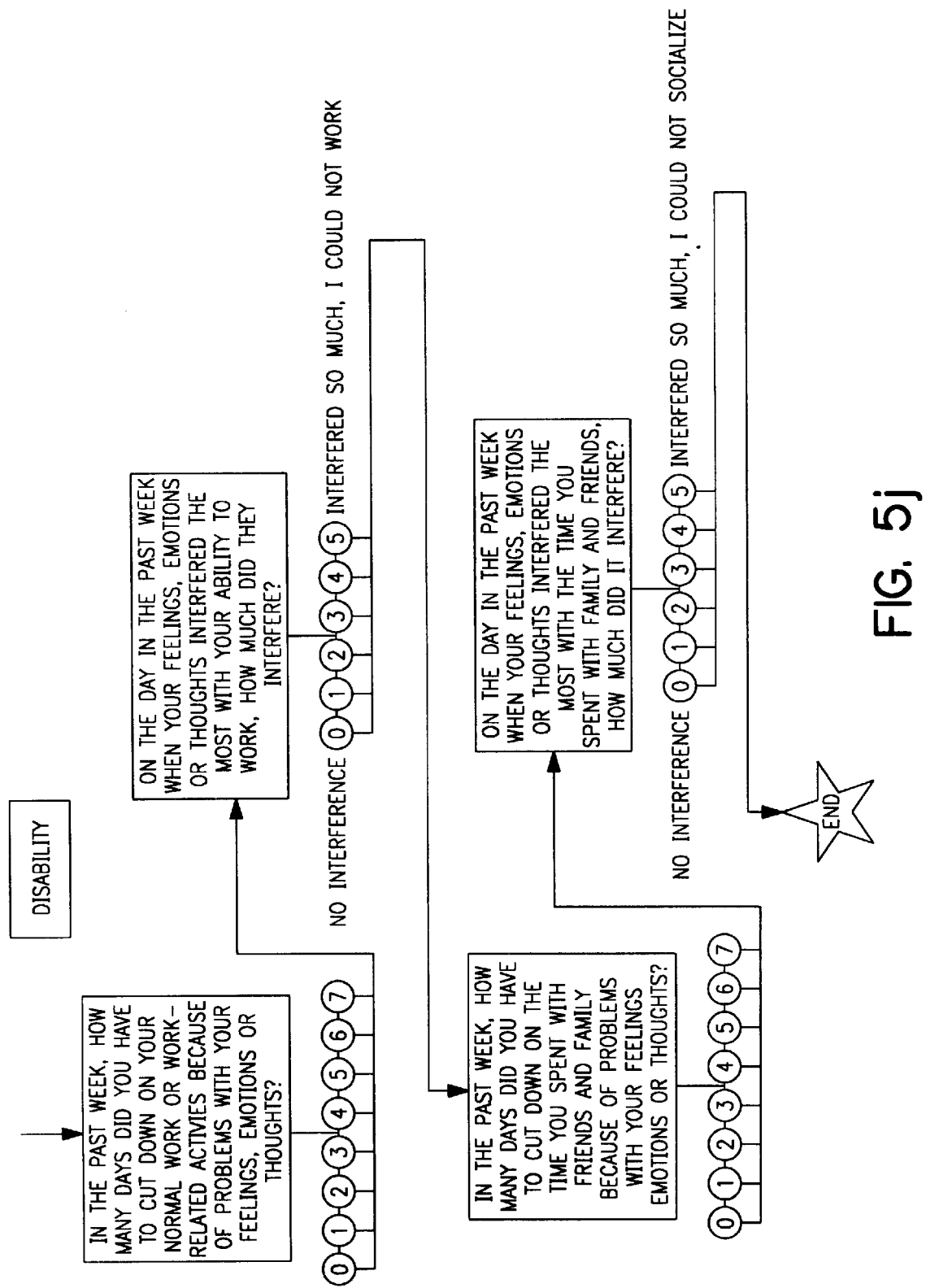

FIGS. 4a–c show a process in which the system suggests diagnostic options based on treatment guidelines retrieved from memory 20. The example in FIGS. 4a–c are for diagnostic guidelines for depression. In block 150 the clinician enters the client's name or ID through the second terminal 24. Alternatively, the clinician can enter the data through the first terminal 22. The computer 26 then displays the client's records, including entered data and suggested treatment guidelines in block 152. The data can be provided to the clinician in a graphical display or other form of organized data compilation. In block 154, the clinician selects a diagnosis(es) displayed on terminal 22 or 24 based on clinical evaluation, including information conveyed via computer. In decision block 156, the process determines whether the diagnosis(es) selected by the clinician deviates from the diagnosis(es) highlighted by the treatment guidelines. If the clinician diagnosis(es) selected in block 154 are consistent with those of the guidelines highlighted in block 152, the process proceeds to block 170 for treatment guidelines. If the clinician diagnosis(es) selected in block 154 deviates from the highlighted guidelines in block 152, the system displays an alert for the clinician, and highlights how clinician's diagnosis deviates from suggested diagnosis in block 158. In decision block 160, the process determines whether the clinician has additional supporting information for chosen diagnosis(es). If the clinician has no additional supporting information, the process proceeds to block 166, wherein the system determines whether the discrepancy requires supervisor approval. If the clinician does have additional information, it is entered in block 162 and clinician confirms diagnosis in decision block 164. If clinician does not confirm diagnosis in block 164, the process stores the sequence in memory 20 for quality review in block 165 and returns to block 152, wherein system highlights suggested diagnosis(es). If clinician does confirm diagnosis(es) in decision block 164, the process determines whether supervisory approval is required in decision block 166. If supervisory approval is not required, the process stores the sequence in memory 20 for quality review in block 168 and proceeds to block 170 for highlighted treatment guidelines. If supervisory approval is required, clinician's supervisor enters a password and sequence is stored in memory 20 for quality review. The process then proceeds to block 170.

In block 170, the system highlights suggested treatments for diagnosis(es) entered in block 154 according to treatment guidelines in memory 20. In block 172, the clinician selects a treatment plan on screen. In decision block 174, the process determines whether the clinician treatment plan is consistent with highlighted treatment guidelines. If the selected treatment is consistent with highlighted guidelines, the process proceeds to specific diagnosis' Treatment Guidelines Module. If the treatment selected by the clinician in block 172 is not consistent with treatment guidelines highlighted in block 170, the system determines whether there are high risk factors which should be taken into consideration for selected treatment in decision block 176 (for example, if suicidality scores are at or above threshold values). If there are high risk factors, the system proceeds to High Risk Module. If the discrepancy in treatment decision is not related to high risk factors, the system determines whether the clinician has additional supporting information for selected treatment plan in decision block 178. If the clinician does not have additional supporting information, the process proceeds to block 182. If the clinician does have additional supporting information, it is entered in block 180. In decision block 182, the process determines whether the discrepancy requires supervisory approval. If the process determines that supervisory approval is not required, it stores the sequence for quality review in memory 20 in block 184 and proceeds to specific diagnosis' Treatment Guidelines Module. If supervisory approval is required, clinician's supervisor enters a password and sequence is stored in memory 20 for quality review.

FIGS. 5a–j show a process for a questionnaire that is provided to the client on the terminal 22. The process includes a plurality of questions which allow the system and medical personnel to determine both a diagnosis and a severity rating for a client. The answers to the questions are used to find a diagnosis according to criteria described in the Diagnostic and Statistical Manual-IV (DSM-IV). Additionally, the quantitative structure of the answers, combined with the DSM-IV criteria allows the clinician to use the same information to measure the severity of the condition, rather than additionally using a separate severity measure, such as the Hamilton Rating Scale for Depression (HRS-D).

Figure 6:
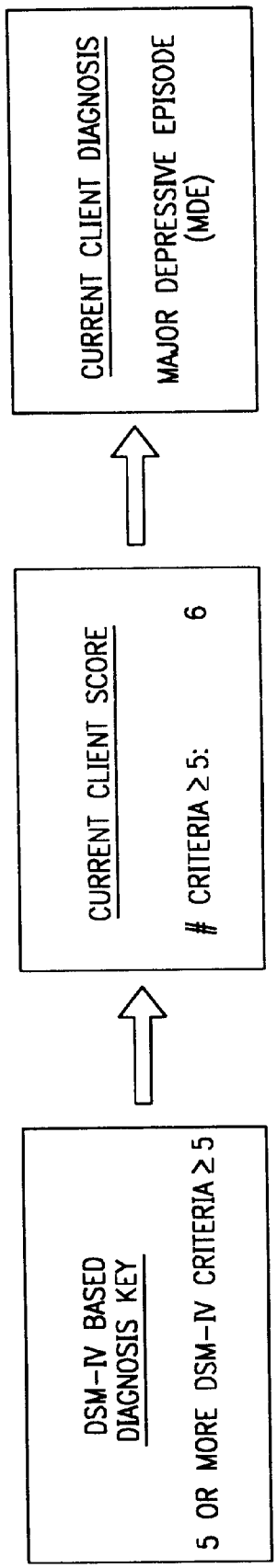
FIG. 6 shows how the system determines a diagnosis.
Figure 7:
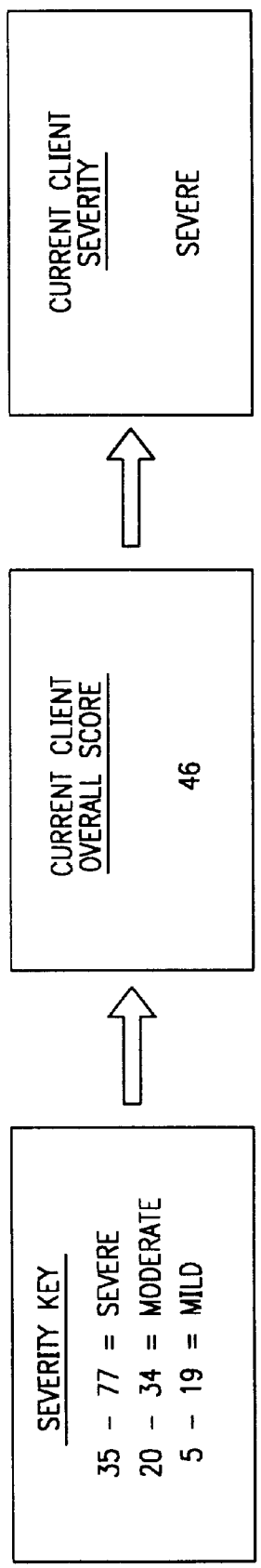
FIG. 7 shows how the system determines severity.

The answers to the questions are stored in the client's personal record. The answers can be compiled and provided in a variety of formats. FIGS. 6 and 7 show examples of how the system determines diagnosis and severity from answers to certain questions regarding depression. FIG. 6 shows how the system determines a diagnosis of depression. The questions are based on DSM-IV criteria for diagnosing Major Depressive Episode (MDE). In the key, the system determines that if 5 or more of the DSM-IV based criteria have a score of $\geq 5$, the client should receive a diagnosis of MDE. The process determines that the current client has 6 criteria for depression that are $\geq 5$ and therefore the client screens positive for Major Depressive Episode (MDE).

FIG. 7 uses the same data to determine the severity of the client's current symptoms. In the key, the system determines cut-off scores for symptom severity. In the example, the client has an overall score of 46 and the system thus establishes a "severe" rating for current symptoms.

Figure 8A:
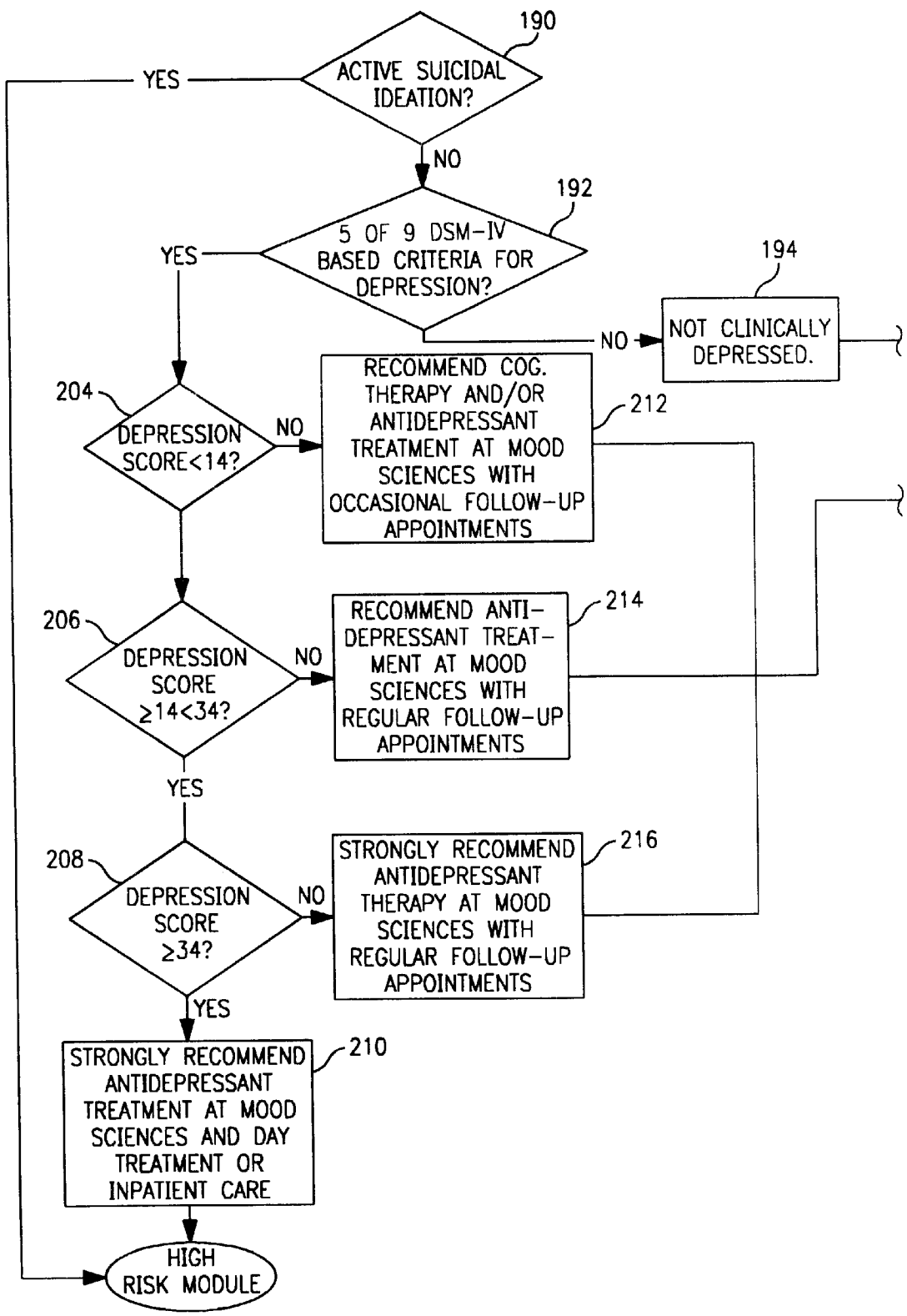
FIG. 8 is a flowchart of treatment guidelines for depression.
Figure 8B:
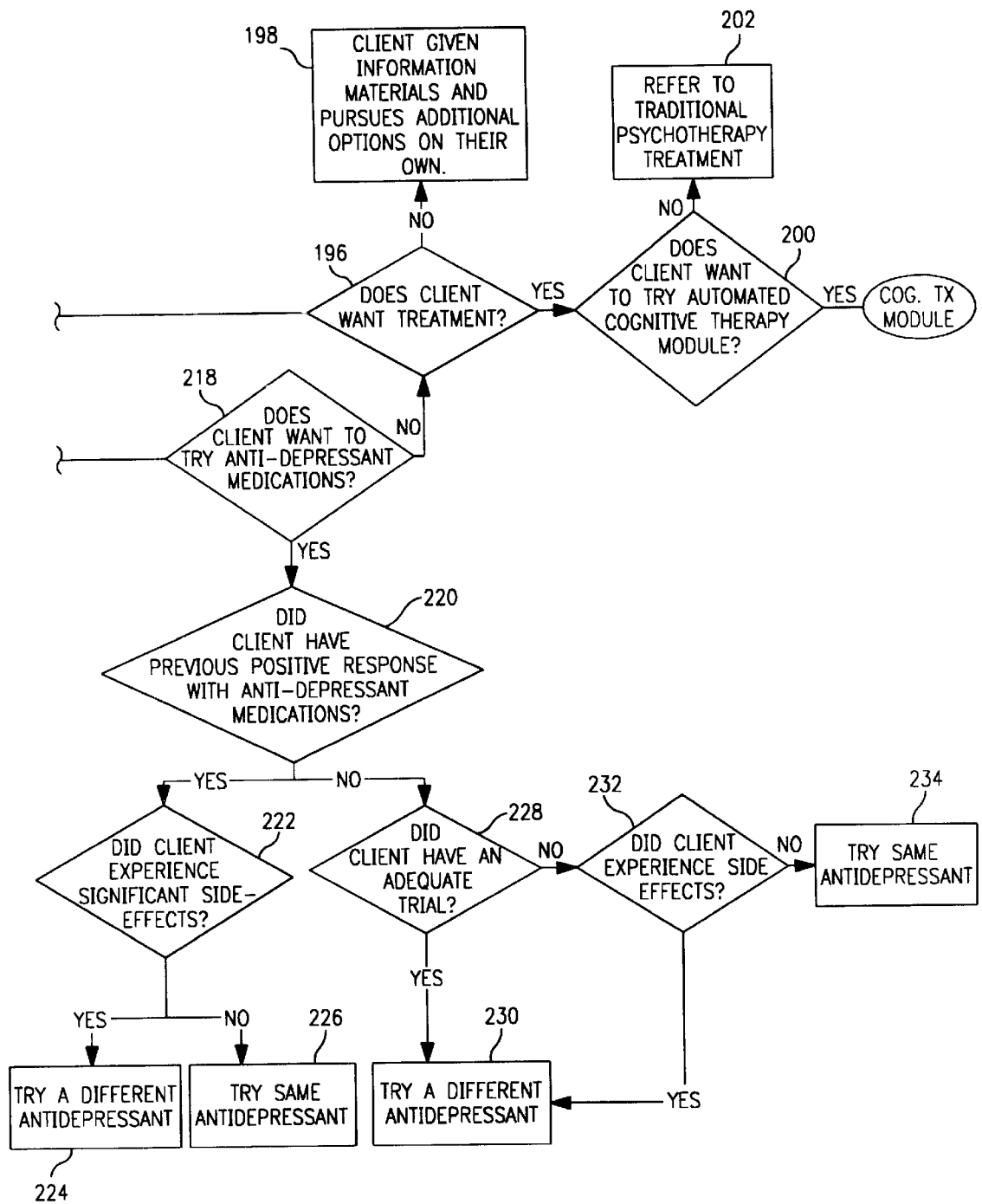

FIG. 8 shows a process that determines a recommended treatment(s) provided to the clinician for specific diagnosis (es). The recommended treatment is based on the client's responses to the questions. In the example in FIG. 8, the process determines whether the client has active suicidal ideation in decision block 190. In decision block 192, the process determines whether the client meets 5 of the 9 DSM-IV based criteria for Major Depression. If less than 5 criteria were determined in decision block 192, the process determines that the client is not clinically depressed in block 194. In decision block 196, the process determines whether the client would still like to receive treatment. If client indicates they do not want treatment, they are given informational materials, which can be downloaded and printed out at the printer 26, and leave the system to pursue other options on their own. If they do want treatment as indicated in decision block 196, the system determines whether they would like to try an automated cognitive therapy module in decision block 200. If client responds affirmatively, the process proceeds to a cognitive therapy module. If the client responds in the negative, he or she is referred to traditional psychotherapy treatment in block 202. Referring to decision block 192, if 5 or more DSM-IV based criteria for depression were met, the process computes a depression score and determines whether the score exceeds a predetermined value in decision blocks 204, 206 and 208. If the client's score is less than or equal to an established cutoff value, the process recommends a specific treatment plan. For example, in FIG. 8, if a client's depression score is calculated at greater than 14, but less than or equal to 21 in decision block 206, the process displays the stored recommended treatment guidelines for that score; in block 214, antidepressant treatment is suggested, with regular follow-up visits. The process then queries the client as to whether they are interested in trying anti-depressant medications in decision block 218. If the client responds in the negative, the process proceeds to decision block 196, wherein client is queried as to whether he or she would like to receive treatment. If client does not want treatment, he or she is given informational material, including data regarding the possibility of symptoms worsening without treatment, and leaves the system to pursue options on their own in block 198. If the clients responds affirmatively in decision block 196, the process proceeds to decision block 200, wherein the client is queried as to whether he or she would like to try an automated cognitive therapy module and proceeds as stated above in block 200. If the client does want to try anti-depressant medications as indicated in decision block 218, the process determines whether client had previous positive response with anti-depressant medications in decision block 220. The process may determine past anti-depressant medication history by getting client response or by checking client's previous response from history questions in block 124. If the process determines that the client had previous positive response with anti-depressant medications, the system queries the client as to whether he or she had significant side effects from the medication in decision block 222 (the process may instead determine whether client had significant side-effects by checking clients' previous response from history questions in block 124). If the client did have significant side effects, the system highlights treatment guideline to try a different antidepressant in block 224. If the client did not have significant side effects, the system highlights treatment guideline to try the same antidepressant in block 226.

Referring to decision block 220, if the process determines that the client did not have a previous positive response with anti-depressant medications, the system determines whether client had an adequate trial in decision block 228. Adequate trial is established from client's history information entered in block 124 and is based on stored guidelines. If the system establishes that the client did have an adequate trial, it highlights the suggested treatment guideline to try a different antidepressant in block 230. If the client did not have an adequate trial as established in decision block 228, the system establishes whether client had significant side effects in decision block 232. If client did not have and adequate trial of previous medication and no significant side effects were established, the system highlights the suggested treatment guideline to try the same antidepressant in block 234.

Figure 9:
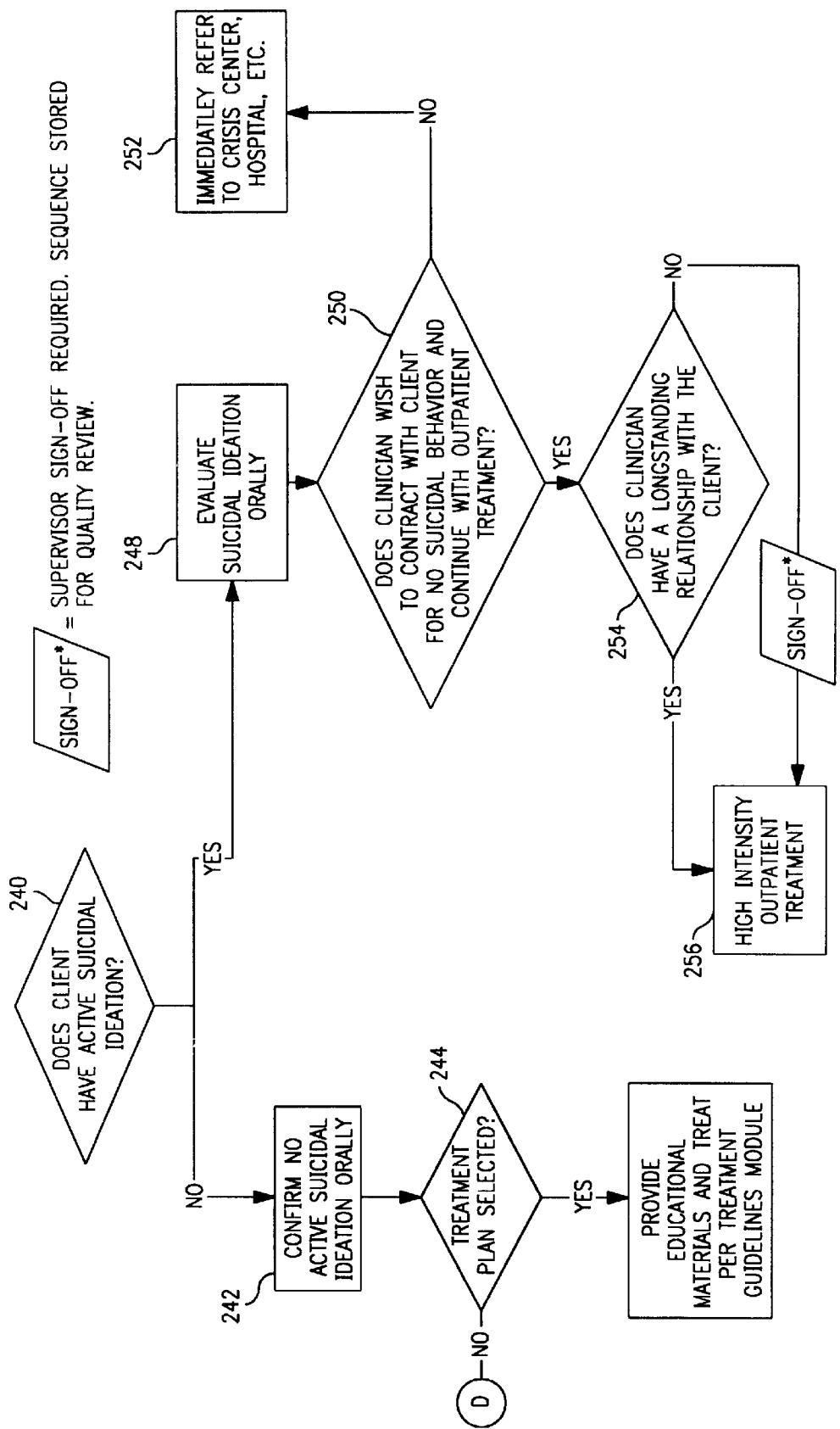
FIG. 9 is a flow chart of guidelines for suicidality.

Referring to decision block 208, if the score is greater than the third threshold, the process proceeds to the High Risk Module. FIG. 9 shows an example of a High Risk Module for suicidality. The system determines whether the client has active suicidal ideation in decision block 240. If the client scores do not show active suicidal ideation, the process proceeds to block 242 to prompt the clinician to confirm no suicidality orally with the client. The system determines whether a treatment plan has been selected in decision block 244 and, if a treatment plan has been selected, the process provides educational material for the client in block 246 which can be downloaded and printed out at the printer 26. If a treatment plan has not yet been selected, the process returns to block 152.

If the client has any active suicidal ideation, the process proceeds to block 248, wherein clinician is prompted to evaluate client's suicidal ideation orally. In decision block 250, the system determines whether the clinician wishes to consider outpatient treatment. If the clinician responds in the negative, the process proceeds to block 252, wherein the client is referred to a crisis center, hospital, etc. If the clinician does wish to consider outpatient treatment, the process determines whether the clinician has a longstanding relationship with the client based on stored guidelines in decision block 254. If the clinician does have a longstanding relationship, the process proceeds to block 256, wherein client is given high-intensity outpatient treatment. If the process determines that the clinician does not have a longstanding relationship with the client in decision block 254, the clinician's supervisor is required to approve decision and the sequence is stored in memory 20 for quality review before proceeding to block 256.

The present invention thus provides a number of computer based processes which can evaluate client conditions and also monitor both the client, and the clinician treating the client.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A computer system for processing medical data, comprising:
    a first terminal that provides a question and receives data from a client in response to the question;
    a second terminal that allows a clinician to review the entered client data and enter a clinician medical decision; and,
    a computer that determines a medical recommendation from a guideline and the client-entered data, and compares the clinician medical decision with the medical recommendation determined by the guideline,
    wherein the computer provides a display of the medical recommendation determined from the guideline.

2. The computer system as recited in claim 1, wherein the clinician medical decision is a treatment.

3. The computer system as recited in claim 2, further comprising a printer connected with the computer.

4. The computer system as recited in claim 3, wherein said computer requires a clinician's supervisor or other provider's supervisor to enter a password before allowing implementation of treatment decisions.

5. The computer system as recited in claim 1, wherein the clinician medical decision is a diagnosis.

6. The computer system as recited in claim 1, wherein said computer provides a query to said second terminal if the medical recommendation determined from the guideline does not match the clinician medical decision.

7. The computer system as recited in claim 1, wherein said computer stores a record in a clinician file if the clinician medical decision does not match the medical recommendation.

8. A method for monitoring a medical decision entered into a computer system, comprising the steps of:
    a) displaying a question on a first terminal;
    b) entering data onto the first terminal in response to the question;
    c) displaying the entered data on a second terminal;
    d) entering a clinician medical decision through the second terminal by a clinician viewing the entered data;
    e) determining a medical recommendation from the data and a guideline;
    f) comparing the medical recommendation with the clinician medical decision; and,
    g) displaying the medical recommendation on the second terminal to the clinician after the data is entered.

9. The method as recited in claim 8, further comprising the step of providing a query to the clinician to reconsider the clinician medical decision if the medical recommendation does not match the clinician medical decision.

10. The method as recited in claim 8, further comprising the steps of entering a prescription and printing the prescription, displaying treatment guidelines for daytreatment options, inpatient and outpatient hospitalization, and other treatment options, including cognitive and behavioral therapies.

11. The method as recited in claim 10, further comprising the step of requiring a password of a clinician's or other provider's supervisor to be entered before allowing an implementation of the clinician medical decisions.

12. The method as recited in claim 8, further comprising the step of storing a record in a clinician file if the clinician medical decision does not match the medical recommendation.

13. A method for determining psychiatric diagnosis and severity of a client's condition by:
    a) displaying a quantitative set of questions on a first terminal;
    b) answering the questions through the first terminal;
    c) determining a psychiatric diagnosis of the patient condition and a severity of the patient condition from the answers in accordance with an algorithm; and,
    d) displaying the diagnosis and the severity on a second terminal.

14. The method as recited in claim 13, wherein the questions are based on DSM-IV criteria.

15. The method as recited in claim 13, further comprising the step of displaying the answers on the second terminal.

* * * * *